(12) United States Patent
Kobori et al.

(10) Patent No.: US 8,084,613 B2
(45) Date of Patent: Dec. 27, 2011

(54) TETRAZOYLOXIME DERIVATIVE AND PLANT DISEASE CONTROL AGENT

(75) Inventors: Takeo Kobori, Inba-gun (JP); Hazumi Nomura, Odawara (JP); Tomoyuki Saiga, Makinohara (JP); Hiroyasu Hosokawa, Fujieda (JP); Ichiro Urihara, Tokyo (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 12/599,854

(22) PCT Filed: May 14, 2007

(86) PCT No.: PCT/JP2008/058844
§ 371 (c)(1),
(2), (4) Date: Nov. 12, 2009

(87) PCT Pub. No.: WO2008/140099
PCT Pub. Date: Nov. 20, 2008

(65) Prior Publication Data
US 2010/0292483 A1 Nov. 18, 2010

(30) Foreign Application Priority Data
May 14, 2007 (JP) .................................. 2007-128053

(51) Int. Cl.
*A61K 31/44* (2006.01)
*C07D 401/00* (2006.01)
(52) U.S. Cl. ..................................... 546/268.4; 514/340
(58) Field of Classification Search .................. None
See application file for complete search history.

(56) References Cited

U.S. PATENT DOCUMENTS
6,340,697 B1 * 1/2002 Kobori et al. ................. 514/364
7,183,299 B2 2/2007 Kobori et al.

FOREIGN PATENT DOCUMENTS
EP 1 184 382 3/2002

OTHER PUBLICATIONS

Silverman, R.B., "The Organic Chemistry of Drug Design and Drug Action," 2004, Elsevier, 2d ed., pp. 29-32.*
Japanese Patent Office, International Search Report (translated) mailed Jul. 15, 2008, from related International Patent Application No. PCT/JP2008/058844.

* cited by examiner

*Primary Examiner* — Janet Andres
*Assistant Examiner* — Heidi Reese

(74) *Attorney, Agent, or Firm* — Kenyon & Kenyon LLP

(57) ABSTRACT

The present invention provides a tetrazoyloxime derivative or salt thereof, represented by the following formula (1):

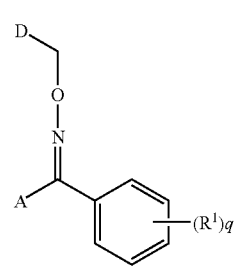

[wherein, $R^1$ represents an optionally substituted C1-C6 alkyl group etc., q represents an integer of 0 to 5, A represents a tetrazoyl group represented by the following formula (2) or (3):

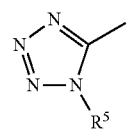

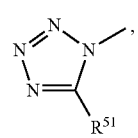

and D represents a group represented by the following formula (4) or (5):

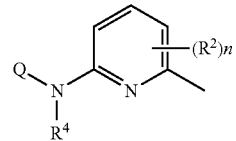

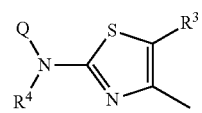

(wherein, $R^2$ represents a halogen atom etc., n represents an integer of 0 to 3, $R^3$ represents a hydrogen atom etc., $R^4$ represents a hydrogen atom etc., Q represents an optionally substituted C1-C20 alkyl group etc.)], and a plant disease control agent.

2 Claims, No Drawings

US 8,084,613 B2

TETRAZOYLOXIME DERIVATIVE AND PLANT DISEASE CONTROL AGENT

TECHNICAL FIELD

The present invention relates to a novel tetrazoyloxime derivative and a plant disease control agent containing the same as an active ingredient thereof.

This application claims priority based on Japanese Patent Application No. 2007-128053, filed in Japan on May 14, 2007, the content of which is incorporated herein by reference.

BACKGROUND ART

In the cultivation of agricultural and horticultural crops, although a large number of control drugs are used against crop disease, since the control effects thereof may be inadequate, the use thereof may be restricted due to the appearance of drug-resistance pathogenic organisms, the plants may be damaged or contaminated by the drug or the drug may demonstrate toxicity to humans, livestock or marine life, a considerable number of these control drugs are not necessarily considered to be satisfactory. Thus, there is a need to develop a plant disease control agent that can be used safely and has few of these shortcomings.

In relation to the present invention, a tetrazoyloxime derivative having a backbone similar to that of the compound of the present invention is reported in Patent Document 1 to be useful as a plant disease control agent.

However, the compound of the present invention is not described in this publication.

Patent Document 1: Japanese Unexamined Patent Application, First Publication No. 2003-137875 (WO 03/016303).

DISCLOSURE OF THE INVENTION

Problems to be Solved by the Invention

An object of the present invention is to provide a tetrazoyloxime derivative, or salt thereof, that causes little chemical damage in useful plants and demonstrates superior pharmacological effects against plant diseases, and to provide a plant disease control agent that contains at least one type of the tetrazoyloxime derivative or salt thereof as an active ingredient thereof.

Means for Solving the Problems

The inventors of the present invention synthesized numerous tetrazoyloxime derivatives and conducted extensive studies of their physiological activity in order to solve the aforementioned problems. As a result, the inventors of the present invention found that a tetrazoyloxime derivative represented by the following formula (1) demonstrates superior control effects against plant disease at low doses while also eliminating concern over chemical damage to useful plants, thereby leading to completion of the present invention.

Thus, according to a first aspect of the present invention, a tetrazoyloxime derivative, or salt thereof, is provided that is represented by the following formula (1):

[Chemical Formula 1]

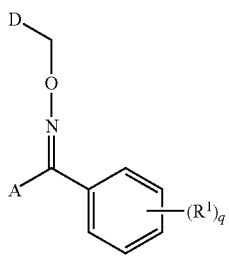

(1)

[wherein, $R^1$ represents a halogen atom, optionally substituted C1-C6 alkyl group, optionally substituted C1-C6 alkoxy group, nitro group, cyano group, optionally substituted aryl group or optionally substituted C1-C6 alkylsulfonyl group, q represents an integer of 0 to 5, $R^1$ may be the same or different when q is 2 or more, A represents a tetrazoyl group represented by the following formula (2) or (3):

[Chemical Formula 2]

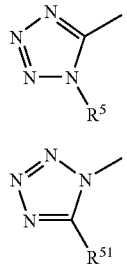

(wherein, $R^5$ and $R^{51}$ represent alkyl groups), and D represents a group represented by the following formula (4) or (5):

[Chemical Formula 3]

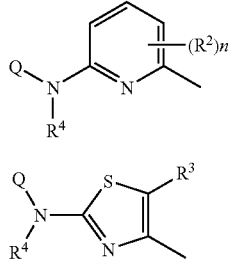

(wherein, $R^2$ represents a halogen atom, optionally substituted C1-C6 alkyl group, optionally substituted C1-C6 alkoxy group, optionally substituted C1-C6 alkylthio group, optionally substituted amino group or optionally substituted aryl group, n represents an integer of 0 to 3, $R^2$ may be the same or different when n is 2 or more, $R^3$ represents a hydrogen atom, halogen atom, optionally substituted C1-C6 alkyl group, optionally substituted C1-C6 alkoxy group, optionally substituted C1-C6 alkylthio group, optionally substituted amino group or optionally substituted aryl group, $R^4$ represents a hydrogen atom, formyl group or unsubstituted or halogen atom-substituted alkylcarbonyl group or alkoxycarbonyl group, and Q represents an optionally substituted C1-C20 alkyl group, optionally substituted C2-C20 alkenyl group, optionally substituted C2-C20 alkynyl group, optionally substituted C3-C8 cycloalkyl group, optionally substituted aralkyl group or optionally substituted heterocycloalkyl group)].

According to a second aspect of the present invention, a plant disease control agent is provided that contains as an active ingredient thereof at least one type of tetrazoyloxime derivative or salt thereof of the present invention.

Effects of the Invention

A plant disease control agent having for an active ingredient thereof the tetrazoyloxime derivative or salt thereof of the present invention demonstrates superior control effects against plant disease at low doses, and eliminates concern over chemical damage to useful plants.

BEST MODE FOR CARRYING OUT THE INVENTION

The following provides a detailed explanation of the present invention by dividing into sections describing 1) a tetrazoyloxime derivative or salt thereof, and 2) a plant disease control agent.

1) Tetrazoyloxime Derivative or Salt Thereof

A first aspect of the present invention is a tetrazoyloxime derivative represented by the aforementioned formula (1), or salt thereof.

In formula (1) above, examples of C1-C6 alkyl group of an optionally substituted C1-C6 alkyl group of $R^1$ include a methyl group, ethyl group, n-propyl group, i-propyl group, n-butyl group, s-butyl group, i-butyl group, t-butyl group, n-pentyl group and n-hexyl group.

There are no particular limitations on substituents of the C1-C6 alkyl group provided they are chemically acceptable substituents, specific examples of which include a hydroxyl group; mercapto group; halogen atom such as a fluorine atom, chlorine atom, bromine atom or iodine atom; cyano group; isocyano group; nitro group; isocyanato group; isothiocyanato group; cyanato group; thiocyanato group; optionally substituted amino groups, including an amino group, methylamino group, benzylamino group, anilino group, dimethylamino group, diethylamino group, phenylethylamino group, an alkylsulfonylamino group such as methylsulfonylamino group, ethylsulfonylamino group, n-propylsulfonylamino group, isopropylsulfonylamino group, n-butylsulfonylamino group or t-butylsulfonylamino group, arylsulfonylamino group such as a phenylsulfonylamino group, heteroarylsulfonylamino group, alkylcarbonylamino group such as a methylcarbonylamino group, ethylcarbonylamino group, n-propylcarbonylamino group or isopropylcarbonylamino group, alkoxycarbonylamino group such as a methoxycarbonylamino group, ethoxycarbonylamino group, n-propoxycarbonylamino group or isopropoxycarbonylamino group, haloalkylsulfonylamino group such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 1,1,1-trifluoroethylsulfonylamino group or pentafluoroethylsulfonylamino group, bis(alkylsulfonyl)amino group such as a bis(methylsulfonyl)amino group, bis(ethylsulfonyl)amino group, (ethylsulfonyl)(methylsulfonyl)amino group, bis(n-propylsulfonyl)amino group, bis(isopropylsulfonyl)amino group, bis(n-butylsulfonyl)amino group or bis(t-butylsulfonyl)amino group, and bis(haloalkylsulfonyl)amino group such as a bis(fluoromethylsulfonyl)amino group, bis(chloromethylsulfonyl)amino group, bis(bromomethylsulfonyl)amino group, bis(difluoromethylsulfonyl)amino group, bis(dichloromethylsulfonyl)amino group, bis(1,1-difluoroethylsulfonyl)amino group, bis(trifluoromethylsulfonyl)amino group, bis(1,1,1-trifluoroethylsulfonyl)amino group or bis(pentafluoroethylsulfonyl)amino group; alkoxy group such as a methoxy group, ethoxy group, n-propoxy group, isopropoxy group, n-butoxy group, s-butoxy group, isobutoxy group or t-butoxy group; alkenyloxy group such as a vinyloxy group or allyloxy group; alkynyloxy group such as an ethynyloxy group or propargyloxy group; aryloxy group such as a phenoxy group or 1-naphthoxy group; aralkyloxy group such as a benzyloxy group or phenethyloxy group; heterocyclooxy group such as a 2-pyridyloxy group or 3-oxazolyloxy group; haloalkoxy group such as a fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 1,1,1-trifluoroethoxy group, pentafluoroethoxy group or hepatafluoro-n-propoxy group; alkylthiocarbonyl group such as a methylthiocarbonyl group, ethylthiocarbonyl group, n-propylthiocarbonyl group, isopropylthiocarbonyl group, n-butylthiocarbonyl group, isobutylthiocarbonyl group, s-butylthiocarbonyl group or t-butylthiocarbonyl group; optionally substituted hydrazino group such as a hydrazino group, N'-phenylhydrazino group, N'-methoxycarbonylhydrazino group, N'-acetylhydrazino group or N'-methylhydrazino group; carboxyl group; alkoxycarbonyl group such as a methoxycarbonyl group, ethoxycarbonyl group, n-propoxycarbonyl group, isopropoxycarbonyl group, n-butoxycarbonyl group or t-butoxycarbonyl group; optionally substituted aminocarbonyl group such as an aminocarbonyl group, dimethylaminocarbonyl group or phenylaminocarbonyl group; optionally substituted hydrazinocarbonyl group such as a hydrazinocarbonyl group, N'-methylhydrazinocarbonyl group or N'-phenylhydrazinocarbonyl group; aryl group such as a phenyl group, 1-naphthyl group or 2-naphthyl group; unsaturated heterocyclic 5-member ring group such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group; unsaturated heterocyclic 6-member ring group such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group or 1,2,4-triazin-3-yl group; saturated heterocyclic group such as a tetrahydrofuran-2-yl group, tetrahydropyran-4-yl group, piperidin-3-yl group, pyrrolidin-2-yl group, morpholino group, piperidino group or N-methylpiperazinyl group; non-N-substituted or N-substituted iminoallyl group such as an N-methylaminoiminomethyl group, 1-N-phenyliminoethyl group, N-hydroxyiminomethyl group or N-methoxyiminomethyl group; non-N-substituted or N-substituted hydrazinocarbonyl group such as an N-methylhydrazinocarbonyl group, N'phenylhydrazinocarbonyl group or hydrazinocarbonyl group; non-N-substituted or N-substituted aminocarbonyl group such as an aminocarbonyl group, dimethylaminocarbonyl group or N-phenyl-N-methylaminocarbonyl group; alkylthio group such as a methylthio group, ethylthio group or t-butylthio group; alkenylthio group such as a vinylthio group or allylthio group; alkynylthio group such as a ethynylthio group or propargylthio group; arylthio group such as a phenylthio group or 4-chlorophenylthio group; heteroarylthio group such as 3 pyridazinylthio group; aralkylthio group such as a benzylthio group or phenethylthio group; alkylsulfonyl group such as a methylsulfonyl group, ethylsulfonyl group or t-butylsulfonyl group; alkenylsulfonyl group such as an allylsulfonyl group; alkynylsulfonyl group such as a propargylsulfonyl group; arylsulfonyl group such as a phenylsulfonyl group; heteroarylsulfonyl group such as a 2-pyridylsulfonyl group or 3-pyridylsulfonyl group; aralkylsulfonyl group such as a benzylsulfonyl group or phenethylsulfonyl group; acyl group such as a formyl group, acetyl group, propionyl group, chloroacetyl group, trifluoroacetyl group, trichloroacetyl group, cinnamoyl group, benzoyl group, 4-chlorobenzoyl group, 2-pyridylcarbonyl group or cyclohexylcarbonyl group; and, acyloxy group such as a formyloxy group, acetyloxy group, propionyloxy group, chloroacetyloxy group, trifluoroacetyloxy group, trichloroacetyloxy group, cinnamoyloxy group, benzoyloxy group, 4-chlorobenzoyloxy group, 2-pyridylcarbonyloxy group or cyclohexylcarbonyloxy group.

Examples of a C1-C6 alkoxy group of an optionally substituted C1-C6 alkoxy group of $R^1$ include a methoxy group, ethoxy group, n-propoxy group, i-propoxy group, n-butoxy group, s-butoxy group, i-butoxy group and t-butoxy group.

There are no particular limitations on substituents of the C1-C6 alkoxy group provided they are chemically acceptable substituents, examples of which include the same substituents as those listed as examples of substituents of C1-C6 alkyl groups.

Examples of halogen atoms of $R^1$ include a fluorine atom, chlorine atom, bromine atom and iodine atom.

Examples of aryl groups of optionally substituted aryl groups of $R^1$ include a phenyl group, 1-naphthyl group and 2-naphthyl group.

There are no particular limitations on substituents of the aryl group provided they are chemically acceptable substituents, specific examples of which include the same substituents as those listed as examples of substituents of C1-C6 alkyl groups, as well as C1-C6 alkyl groups such as a methyl group, ethyl group, n-propyl group, i-propyl group, n-butyl group, s-butyl group, i-butyl group, t-butyl group, n-pentyl group or n-hexyl group; C2-C6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; C2-C6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; haloalkyl groups such as a chloromethyl group, fluoromethyl group, bromomethyl group, dichloromethyl group, difluoromethyl group, dibromomethyl group, trichloromethyl group, trifluoromethyl group, bromodifluoromethyl group, 1,1,1-trifluoroethyl group, 1-chloroethyl group, 2-chloroethyl group, 1-bromoethyl group or pentafluoroethyl group; aralkyl groups such as a benzyl group or phenethyl group; unsaturated heterocyclic 5-member ring alkyl groups such as a 5-phenyl-5-trifluoromethyl-isooxazolin-3-yl group, 2-furfurylmethyl group, 3-thienylmethyl group or 1-methyl-3-pyrazolomethyl group; unsaturated heterocyclic 6-member ring alkyl groups such as a 2-pyridylmethyl group, 3-pyridylmethyl group, 6-chloro-3-pyridylmethyl group or 2-pyrimidylmethyl group; and saturated heterocyclic alkyl groups such as a 2-tetrahydrofuranyl group, 3-piperazylmethyl group, N-methyl-3-pyrrolidylmethyl group or morpholinomethyl group.

Examples of C1-C6 alkylsulfonyl groups of $R^1$ include a methylsulfonyl group and an ethylsulfonyl group. Examples of substituents of the alkylsulfonyl groups include the same substituents as those listed as examples of substituents of C1-C6 alkyl groups.

q represents an integer of 0 to 5 and is preferably 0 or 1.

Specific examples of alkyl groups of $R^5$ in formula (2) and $R^{51}$ in formula (3) include a methyl group, ethyl group, n-propyl group, i-propyl group, n-butyl group, s-butyl group, i-butyl group, t-butyl group, n-pentyl group and n-hexyl group, with C1-C3 alkyl groups being particularly preferable.

Specific examples of halogen atoms and optionally substituted C1-C6 alkyl groups of $R^2$ in formula (4) and $R^3$ in formula (5) include the same functional groups as those listed as example of $R^1$ above. Specific examples of optionally substituted C1-C6 alkoxy groups of $R^2$ and $R^3$ include functional groups listed as examples of $R^1$ having 1 to 6 carbon atoms. Specific examples of C1-C6 alkylthio groups of the optionally substituted C1-C6 alkylthio groups of $R^2$ and $R^3$ include a methylthio group, ethylthio group, n-propylthio group and isopropylthio group. Examples of substituents of C1-C6 alkylthio groups include the same substituents listed as examples of substituents of C1-C6 alkyl groups of $R^1$.

Specific examples of optionally substituted amino groups of $R^2$ and $R^3$ include an amino group, methylamino group, dimethylamino group, ethylamino group, diethylamino group and methylethylamino group, as well as amino groups having the same substituents as those listed as examples of substituents of aryl groups of $R^1$ that are within a chemically acceptable range.

Specific examples of optionally substituted aryl groups of $R^2$ and $R^3$ include the same functional groups as those listed as examples of $R^1$.

Specific examples of unsubstituted or halogen atom-substituted alkylcarbonyl groups of $R^4$ include an acetyl group, propionyl group, chloroacetyl group, trichloroacetyl group, trifluoroacetyl group and pentafluoropropionyl group. Specific examples of alkoxycarbonyl groups include a methoxycarbonyl group, ethoxycarbonyl group, n-propoxycarbonyl group, isopropoxycarbonyl group, n-butoxycarbonyl group and t-butoxycarbonyl group.

Examples of C1-C20 alkyl groups of the optionally substituted C1-C20 alkyl group of Q include a methyl group, ethyl group, n-propyl group, i-propyl group, n-butyl group, s-butyl group, i-butyl group, t-butyl group, n-pentyl group, n-hexyl group, n-octyl group and n-nonyl group.

Specific examples of C2-C20 alkenyl groups of the optionally substituted C2-C20 alkenyl group of Q include C2-C6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; and, an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and stearyl group.

Specific examples of C2-C20 alkynyl groups of the optionally substituted C2-C20 alkynyl group of Q include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Examples of C3-C8 cycloalkyl groups of the optionally substituted C3-C8 cycloalkyl group of Q include a cyclopropyl group, cyclobutyl group, cyclopentyl group, cyclohexyl group, cyclooctyl group and 4-methylcyclohexyl group.

There are no particular limitations on substituents of the optionally substituted C1-C20 alkyl group, optionally substituted C2-C20 alkenyl group, optionally substituted C2-C20 alkynyl group and optionally substituted C3-C8 cycloalkyl group of Q provided they are chemically acceptable substituents, and examples include the same substituents as those listed as examples of substituents of the C1-C6 alkyl group of $R^1$.

Specific examples of aralkyl groups of the optionally substituted aralkyl group of Q include a benzyl group, phenethyl group and 1-naphthylmethyl group. Examples of substituents of the aralkyl group include the same substituents as those listed as examples of substituents of the aryl group of $R^1$.

Specific examples of heterocyclic alkyl groups of the optionally substituted heterocyclic alkyl group of Q include unsaturated heterocyclic 5-member alkyl groups such as a 5-phenyl-5-trifluoromethyl-isoxazolin-3-yl group, 2-furfurylmethyl group, 3-thienylmethyl group and 1-methyl-3-pyrazolomethyl group; unsaturated heterocyclic 6-member alkyl groups such as a 2-pyridylmethyl group, 3-pyridylmethyl group, 6-chloro-3-pyridylmethyl group and 2-pyrimidylmethyl group; and saturated heterocyclic alkyl groups such as a 2-tetrahydrofuranylmethyl group, 3-piperazylmethyl group, N-methyl-3-pyrrolidylmethyl group and morpholinomethyl group. Examples of substituents of heterocyclic alkyl groups include the same substituents as those listed as examples of substituents of the aryl group of $R^1$.

(E)-form and (Z)-form stereoisomers exist for the oxime moiety present in the tetrazoyloxime derivative represented by the aforementioned formula (1) based on carbon-nitrogen double bonds. These two stereoisomers along with mixtures thereof are also included in the present invention. Synthetic products are normally obtained in the form of the (Z)-form only or as a mixture of the (E)-form and (Z)-form. The two isomers can be respectively isolated from a mixture of the (E)-form and (Z)-form by separating in accordance with known techniques.

In addition, there are no particular limitations on salts of the compound represented by the aforementioned formula (1) provided they are agriculturally and horticulturally acceptable salts, examples of which include salts of inorganic acids such as hydrochlorides, nitrates, sulfates or phosphates; and salts of organic acids such as acetates, lactates, propionates, benzoates, trifluoromethane sulfonate, tosylates, salicylates or 1-naphthoates.

The (Z)-form of the tetrazoyloxime derivative represented by the aforementioned formula (1), or salts thereof, has superior plant disease control effects as compared with the (E)-form. However, since the (Z)-form is partially converted to the (E)-form due to the action of light and the like in the natural environment, and tends to stabilize at a constant ratio in the form of a mixture of the (E)-form and the (Z)-form, both of these compounds as well as mixtures thereof are useful. Furthermore, since the stable ratio of the (E)-form to the (Z)-form varies according to individual compounds, it cannot be universally specified.

(Production Method)

There are no particular limitations on the method used to produce the compound represented by the aforementioned formula (1), and can be produced according to, for example, the method indicated below.

A compound represented by the following formula (1-1), in which D is a group represented by formula (4) and $R^4$ is not a hydrogen atom in the aforementioned formula (1) can be obtained by reacting a compound represented by formula (7) with a compound represented by formula (6) in the presence of a base. Moreover, a compound represented by the following formula (1-2) in which D is a group represented by formula (4) and $R^4$ is a hydrogen atom in formula (1) can be obtained by allowing an acid to act on the resulting compound represented by formula (1-1).

[Chemical Formula 4]

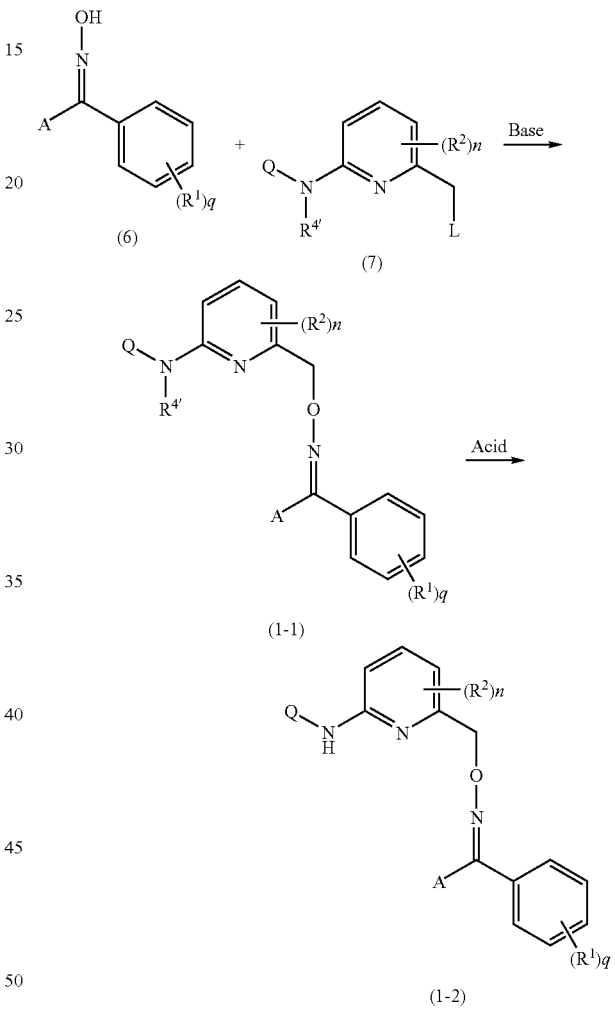

(In the above formula, A, Q, $R^1$, $R^2$, n and q are the same as previously defined, L represents a leaving group such as a halogen atom, and $R^{4'}$ is an $R^4$ group other than a hydrogen atom.)

Examples of base used in the reaction between a compound represented by formula (6) and a compound represented by formula (7) include inorganic bases such as sodium hydroxide, sodium hydride, potassium hydroxide, sodium carbonate or potassium carbonate; and, organic bases such as triethylamine, 4-(dimethylamino)pyridine or pyridine.

One type of these bases can be used alone or two or more types can be used in combination.

The amount of base used is normally 0.01 to 20 times moles and preferably 0.1 to 5 times moles based on the compound represented by formula (6).

This reaction can be carried out in the presence or absence of a solvent.

There are no particular limitations on the solvent used provided it is an inert solvent in the reaction. Examples of solvents include hydrocarbon-based solvents such as pentane, hexane, heptane, benzene, toluene or xylene; halogen-based solvents such as dichloromethane, chloroform, hydrocarbon tetrachloride; nitrile-based solvents such as acetonitrile or propionitrile; ether-based solvents such as diethyl ether, dioxane or tetrahydrofuran; amide-based solvents such as N,N-dimethylformamide, N,N-dimethylacetoamide or N-methylpyrrolidone; sulfoxide-based solvents such as dimethylsulfoxide; water; and mixed solvents thereof.

The reaction temperature of this reaction is normally −70 to +200° C. and preferably −20 to +100° C.

Although varying according to the reaction scale and the like, the reaction time is normally within the range of 30 minutes to 24 hours.

Examples of acids used in the reaction for obtaining a compound represented by formula (1-2) from a compound represented by formula (1-1) include inorganic acids such as hydrogen chloride, hydrochloric acid, sulfuric acid, nitric acid or phosphoric acid; and organic acids such as acetic acid, trifluoroacetic acid or p-toluenesulfonic acid.

The amount of acid used is normally 0.01 to 100 times moles and preferably 0.1 to 25 times moles based on the compound represented by formula (1-1).

This reaction can be carried out in the presence or absence of a solvent. The solvent used is not limited to the inert solvent used in the present reaction, and examples include the same solvents listed as examples of solvents able to be used in the reaction for obtaining a compound represented by the aforementioned formula (1-1).

The reaction temperature of this reaction is normally within the range of −70 to +200° C. and preferably −20 to +100° C.

Although varying according to the reaction scale and the like, the reaction time is normally within the range of 30 minutes to 24 hours.

In addition, a salt of a compound represented by the aforementioned formula (1) can be produced allowing an acid to act on a compound represented by formula (1) in accordance with ordinary methods.

In either of these reactions, the target compound can be isolated by carrying out an ordinary post-treatment operation following completion of the reaction. In addition, if purification of the product is required, known, commonly used purification means can be employed such as distillation, recrystallization or column chromatography.

Specific examples of tetrazoyloxime derivatives represented by formula (1) that are produced in the manner described above are shown in the following TABLES 1 to 4.

TABLE 1

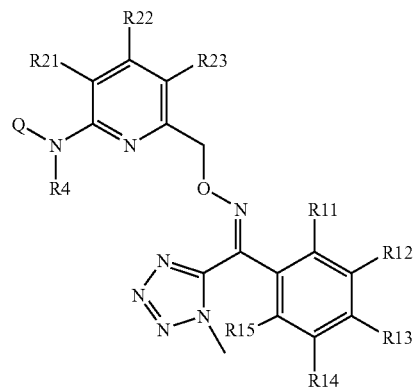

| Compound No. | Q | R4 | R21 | R22 | R23 | R11 | R12 | R13 | R14 | R15 |
|---|---|---|---|---|---|---|---|---|---|---|
| I-1 | $CH_3$ | H | H | H | H | H | H | H | H | H |
| I-2 | $CH_3CH_2$ | H | H | H | H | H | H | H | H | H |
| I-3 | $CH_3(CH_2)_2$ | H | H | H | H | H | H | H | H | H |
| I-4 | $CH_3(CH_2)_3$ | H | H | H | H | H | H | H | H | H |
| I-5 | $(CH_3)_2CHCH_2$ | H | H | H | H | H | H | H | H | H |
| I-6 | $CH_3(CH_2)_4$ | H | H | H | H | H | H | H | H | H |
| I-7 | $(CH_3CH_2)_2CH$ | H | H | H | H | H | H | H | H | H |
| I-8 | $CH_3(CH_2)_5$ | H | H | H | H | H | H | H | H | H |
| I-9 | $CH_3(CH_2)_6$ | H | H | H | H | H | H | H | H | H |
| I-10 | $CH_3(CH_2)_7$ | H | H | H | H | H | H | H | H | H |
| I-11 | $H_2C=CHCH_2$ | H | H | H | H | H | H | H | H | H |
| I-12 | $HC\equiv CCH_2$ | H | H | H | H | H | H | H | H | H |
| I-13 | $CH_3C\equiv CCH_2$ | H | H | H | H | H | H | H | H | H |
| I-14 | $CF_3CH_2$ | H | H | H | H | H | H | H | H | H |
| I-15 | $NCCH_2$ | H | H | H | H | H | H | H | H | H |
| I-16 | $NC(CH_2)_2$ | H | H | H | H | H | H | H | H | H |
| I-17 | $NC(CH_2)_3$ | H | H | H | H | H | H | H | H | H |
| I-18 | $NC(CH_2)_4$ | H | H | H | H | H | H | H | H | H |
| I-19 | $C_6H_5CH_2$ | H | H | H | H | H | H | H | H | H |
| I-20 | $C_6H_5(CH_2)_2$ | H | H | H | H | H | H | H | H | H |
| I-21 | $C_6H_5(CH_2)_3$ | H | H | H | H | H | H | H | H | H |
| I-22 | $C_6H_5(CH_2)_4$ | H | H | H | H | H | H | H | H | H |
| I-23 | $4-CF_3C_6H_4CH_2$ | H | H | H | H | H | H | H | H | H |
| I-24 | $4-CH_3O-C_6H_4(CH_2)_2$ | H | H | H | H | H | H | H | H | H |

TABLE 1-continued

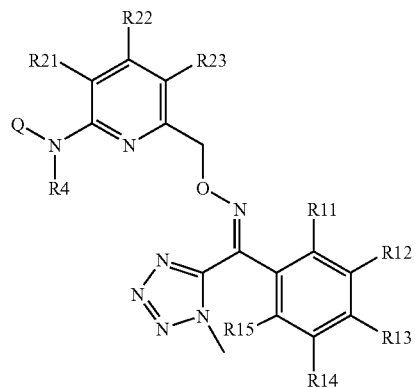

| Compound No. | Q | R4 | R21 | R22 | R23 | R11 | R12 | R13 | R14 | R15 |
|---|---|---|---|---|---|---|---|---|---|---|
| I-25 | (CH$_3$)$_3$CC(=O)CH$_2$ | H | H | H | H | H | H | H | H | H |
| I-26 | CH$_3$CH$_2$OC(=O)CH$_2$ | H | H | H | H | H | H | H | H | H |
| I-27 | HOC(=O)CH$_2$ | H | H | H | H | H | H | H | H | H |
| I-28 | H$_2$N(CH$_2$)$_3$ | H | H | H | H | H | H | H | H | H |
| I-29 | 2-Pyridylmethyl | H | H | H | H | H | H | H | H | H |
| I-30 | 3-Pyridylmethyl | H | H | H | H | H | H | H | H | H |
| I-31 | 2-amino-6-pyridylmethyl | H | H | H | H | H | H | H | H | H |
| I-32 | 4-pyridylmethyl | H | H | H | H | H | H | H | H | H |
| I-33 | 2-chloro-5-pyridylmethyl | H | H | H | H | H | H | H | H | H |
| I-34 | 2-(2-amino-6-pyridylmethyl)amino-6-pyridylmethyl | H | H | H | H | H | H | H | H | H |
| I-35 | 4-(CH$_3$)$_2$NC$_6$H$_4$CH$_2$ | H | H | H | H | H | H | H | H | H |
| I-36 | 4-CH$_3$OC$_6$H$_4$CH$_2$ | H | H | H | H | H | H | H | H | H |
| I-37 | C$_6$H$_5$CH=CHCH$_2$ | H | H | H | H | H | H | H | H | H |
| I-38 | CH$_3$OCH$_2$ | H | H | H | H | H | H | H | H | H |
| I-39 | CH$_3$OCH$_2$CH$_2$ | H | H | H | H | H | H | H | H | H |
| I-40 | CH$_3$SCH$_2$ | H | H | H | H | H | H | H | H | H |
| I-41 | CH$_3$SCH$_2$CH$_2$ | H | H | H | H | H | H | H | H | H |
| I-42 | ClCH$_2$CH$_2$ | H | H | H | H | H | H | H | H | H |
| I-43 | Cl$_3$CCH$_2$ | H | H | H | H | H | H | H | H | H |
| I-44 | 3-Iodopropargyl | H | H | H | H | H | H | H | H | H |
| I-45 | C$_6$H$_5$OCH$_2$CH$_2$ | H | H | H | H | H | H | H | H | H |
| I-46 | C$_6$H$_5$CH$_2$OCH$_2$CH$_2$ | H | H | H | H | H | H | H | H | H |
| I-47 | I$_2$C=ClCH$_2$ | H | H | H | H | H | H | H | H | H |
| I-48 | (CH$_3$)$_2$NNHCH$_2$CH$_2$ | H | H | H | H | H | H | H | H | H |
| I-49 | cyclopropyl | H | H | H | H | H | H | H | H | H |
| I-50 | cyclohexyl | H | H | H | H | H | H | H | H | H |
| I-51 | 3-methyl-5-isoxazolyl | H | H | H | H | H | H | H | H | H |
| I-52 | 2-1,3-dimethyl-5-pyrazolyloxy)ethyl | H | H | H | H | H | H | H | H | H |
| I-53 | 2-(3-methyl-5-isoxazolylthio)ethyl | H | H | H | H | H | H | H | H | H |
| II-1 | CH$_3$(CH$_2$)$_4$ | H | H | H | Cl | H | H | H | H | H |
| II-2 | CH$_3$(CH$_2$)$_4$ | H | H | Cl | H | H | H | H | H | H |
| II-3 | CH$_3$(CH$_2$)$_4$ | H | H | CH$_3$S | H | H | H | H | H | H |
| II-4 | CH$_3$(CH$_2$)$_4$ | H | H | CH$_3$NH | H | H | H | H | H | H |
| II-5 | CH$_3$(CH$_2$)$_4$ | H | H | (CH$_3$)$_2$CH | H | H | H | H | H | H |
| II-6 | CH$_3$(CH$_2$)$_4$ | H | H | H | Br | H | H | H | H | H |
| II-7 | CH$_3$(CH$_2$)$_4$ | H | Br | H | H | H | H | H | H | H |
| II-8 | CH$_3$(CH$_2$)$_4$ | H | Br | H | Br | H | H | H | H | H |
| II-9 | CH$_3$(CH$_2$)$_4$ | H | H | Me | H | H | H | H | H | H |
| II-10 | CH$_3$(CH$_2$)$_4$ | H | H | H | Me | H | H | H | H | H |
| II-11 | CH$_3$(CH$_2$)$_4$ | H | H | (CH$_3$)$_3$C | H | H | H | H | H | H |
| II-12 | CH$_3$(CH$_2$)$_4$ | H | H | H | Ph | H | H | H | H | H |
| II-13 | CH$_3$(CH$_2$)$_4$ | H | 4-ClC$_6$H$_4$ | H | 4-ClC$_6$H$_4$ | H | H | H | H | H |
| II-14 | CH$_3$(CH$_2$)$_4$ | H | H | CH$_3$O | H | H | H | H | H | H |
| II-15 | CH$_3$(CH$_2$)$_4$ | H | H | CH$_3$CH$_2$O | H | H | H | H | H | H |
| II-16 | CH$_3$(CH$_2$)$_4$ | H | H | (CH$_3$)$_2$CHO | H | H | H | H | H | H |
| II-17 | CH$_3$(CH$_2$)$_4$ | H | H | CH$_3$CH$_2$O(CH$_2$)$_2$O | H | H | H | H | H | H |
| II-18 | CH$_3$(CH$_2$)$_4$ | H | H | (CH$_3$)$_2$N | H | H | H | H | H | H |

TABLE 1-continued

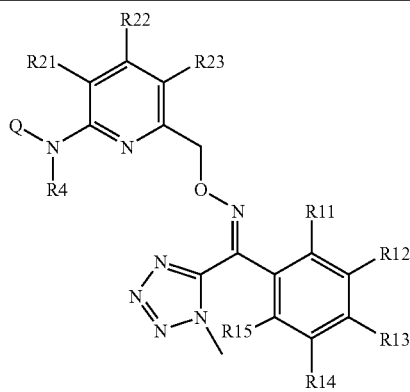

| Compound No. | Q | R4 | R21 | R22 | R23 | R11 | R12 | R13 | R14 | R15 |
|---|---|---|---|---|---|---|---|---|---|---|
| II-19 | 2-n-butylamino-4-isopropyl-6-pyridylmethyl | H | H | $(CH_3)_2CH$ | H | H | H | H | H | H |
| III-1 | $CH_3(CH_2)_4$ | H | H | H | H | F | H | H | H | H |
| III-2 | $CH_3(CH_2)_3$ | H | H | H | H | H | F | H | H | H |
| III-3 | $CH_3(CH_2)_4$ | H | H | H | H | H | F | H | H | H |
| III-4 | $CH_3(CH_2)_5$ | H | H | H | H | H | F | H | H | H |
| III-5 | $(CH_3)_2CHCH_2$ | H | H | H | H | H | F | H | H | H |
| III-6 | $C_6H_5CH_2CH_2$ | H | H | H | H | H | F | H | H | H |
| III-7 | $CH_3C\equiv CCH_2$ | H | H | H | H | H | F | H | H | H |
| III-8 | $CH_3(CH_2)_4$ | H | H | H | H | F | H | H | H | F |
| III-9 | $CH_3(CH_2)_4$ | H | H | H | H | H | H | F | H | H |
| III-10 | $CH_3(CH_2)_4$ | H | H | H | H | F | F | H | H | H |
| III-11 | $CH_3(CH_2)_4$ | H | H | H | H | F | H | F | H | H |
| III-12 | $CH_3(CH_2)_4$ | H | H | H | H | H | F | F | H | H |
| III-13 | $CH_3(CH_2)_4$ | H | H | H | H | F | H | H | F | H |
| III-14 | $CH_3(CH_2)_4$ | H | H | H | H | F | F | $CH_3$ | H | H |
| III-15 | $CH_3(CH_2)_4$ | H | H | H | H | F | F | H | F | H |
| III-16 | $CH_3(CH_2)_4$ | H | H | H | H | F | H | H | H | F |
| III-17 | $CH_3(CH_2)_4$ | H | H | H | H | F | H | F | F | H |
| III-18 | $CH_3(CH_2)_4$ | H | H | H | H | F | H | F | H | F |
| III-19 | $CH_3(CH_2)_4$ | H | H | H | H | F | F | F | H | H |
| III-20 | $CH_3(CH_2)_4$ | H | H | H | H | F | F | F | H | F |
| III-21 | $CH_3(CH_2)_4$ | H | H | H | H | F | F | H | F | F |
| III-22 | $CH_3(CH_2)_4$ | H | H | H | H | F | F | F | F | F |
| III-23 | $CH_3(CH_2)_4$ | H | H | H | H | $CH_3$ | H | H | H | H |
| III-24 | $CH_3(CH_2)_4$ | H | H | H | H | H | $CH_3$ | H | H | H |
| III-25 | $CH_3(CH_2)_4$ | H | H | H | H | H | H | $CH_3$ | H | H |
| III-26 | $CH_3(CH_2)_4$ | H | H | H | H | $CH_3$ | $CH_3$ | H | H | H |
| III-27 | $CH_3(CH_2)_4$ | H | H | H | H | $CH_3$ | H | $CH_3$ | H | H |
| III-28 | $CH_3(CH_2)_4$ | H | H | H | H | H | $CH_3$ | $CH_3$ | H | H |
| III-29 | $CH_3(CH_2)_4$ | H | H | H | H | $CH_3$ | H | H | $CH_3$ | H |
| III-30 | $CH_3(CH_2)_4$ | H | H | H | H | $CH_3$ | H | H | H | $CH_3$ |
| III-31 | $CH_3(CH_2)_4$ | H | H | H | H | $CH_3$ | $CH_3$ | $CH_3$ | H | H |
| III-32 | $CH_3(CH_2)_4$ | H | H | H | H | $CH_3$ | $CH_3$ | H | $CH_3$ | H |
| III-33 | $CH_3(CH_2)_4$ | H | H | H | H | $CH_3$ | $CH_3$ | H | H | $CH_3$ |
| III-34 | $CH_3(CH_2)_4$ | H | H | H | H | $CH_3$ | H | $CH_3$ | $CH_3$ | H |
| III-35 | $CH_3(CH_2)_4$ | H | H | H | H | $CH_3$ | H | $CH_3$ | H | $CH_3$ |
| III-36 | $CH_3(CH_2)_4$ | H | H | H | H | $CH_3$ | $CH_3$ | $CH_3$ | $CH_3$ | H |
| III-37 | $CH_3(CH_2)_4$ | H | H | H | H | $CH_3$ | $CH_3$ | $CH_3$ | H | $CH_3$ |
| III-38 | $CH_3(CH_2)_4$ | H | H | H | H | $CH_3$ | $CH_3$ | H | $CH_3$ | $CH_3$ |
| III-39 | $CH_3(CH_2)_4$ | H | H | H | H | $CH_3$ | $CH_3$ | $CH_3$ | $CH_3$ | $CH_3$ |
| III-40 | $CH_3(CH_2)_4$ | H | H | H | H | $CF_3$ | H | H | H | H |
| III-41 | $CH_3(CH_2)_4$ | H | H | H | H | H | $CF_3$ | H | H | H |
| III-42 | $CH_3(CH_2)_4$ | H | H | H | H | H | H | $CF_3$ | H | H |
| III-43 | $CH_3(CH_2)_4$ | H | H | H | H | $CF_3$ | H | Cl | H | H |
| III-44 | $CH_3(CH_2)_4$ | H | H | H | H | $CF_3$ | H | H | F | F |
| III-45 | $CH_3(CH_2)_4$ | H | H | H | H | $CF_3O$ | H | H | H | H |
| III-46 | $CH_3(CH_2)_4$ | H | H | H | H | H | $CF_3O$ | H | H | H |
| III-47 | $CH_3(CH_2)_4$ | H | H | H | H | H | H | $CF_3O$ | H | H |
| III-48 | $CH_3(CH_2)_4$ | H | H | H | H | $CF_3O$ | H | Cl | H | H |
| III-49 | $CH_3(CH_2)_4$ | H | H | H | H | $CF_3O$ | H | H | F | F |
| IV-1 | $CH_3(CH_2)_3$ | CHO | H | H | H | H | H | H | H | H |
| IV-2 | $(CH_3)_2CHCH_2$ | CHO | H | H | H | H | H | H | H | H |
| IV-3 | $CH_3(CH_2)_4$ | CHO | H | H | H | H | H | H | H | H |
| IV-4 | $CH_3(CH_2)_5$ | CHO | H | H | H | H | H | H | H | H |
| IV-5 | $CH_3(CH_2)_6$ | CHO | H | H | H | H | H | H | H | H |
| IV-6 | $H_2C\!=\!CHCH_2$ | CHO | H | H | H | H | H | H | H | H |

TABLE 1-continued

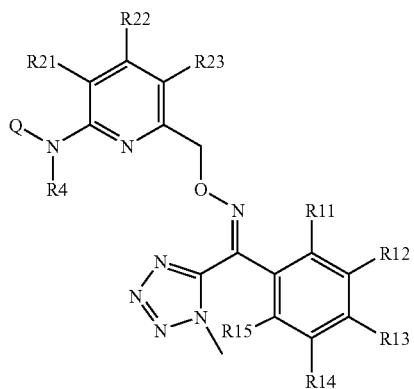

| Compound No. | Q | R4 | R21 | R22 | R23 | R11 | R12 | R13 | R14 | R15 |
|---|---|---|---|---|---|---|---|---|---|---|
| IV-7 | HC≡CCH$_2$ | CHO | H | H | H | H | H | H | H | H |
| IV-8 | CH$_3$≡CCH$_2$ | CHO | H | H | H | H | H | H | H | H |
| IV-9 | C$_6$H$_5$CH$_2$ | CHO | H | H | H | H | H | H | H | H |
| IV-10 | C$_6$H$_5$(CH$_2$)$_2$ | CHO | H | H | H | H | H | H | H | H |
| IV-11 | C$_6$H$_5$(CH$_2$)$_3$ | CHO | H | H | H | H | H | H | H | H |
| IV-12 | CH$_3$CH$_2$OC(=O)CH$_2$ | CHO | H | H | H | H | H | H | H | H |
| IV-13 | NCCH$_2$ | CHO | H | H | H | H | H | H | H | H |
| IV-14 | 2-pyridylmethyl | CHO | H | H | H | H | H | H | H | H |
| IV-15 | 4-pyridylmethyl | CHO | H | H | H | H | H | H | H | H |
| IV-16 | 2-chloro-5-pyridylmethyl | CHO | H | H | H | H | H | H | H | H |
| IV-17 | CH$_3$(CH$_2$)$_4$ | CF$_3$CO | H | H | H | H | H | H | H | H |
| IV-18 | CH$_3$(CH$_2$)$_4$ | C$_2$F$_5$CO | H | H | H | H | H | H | H | H |
| IV-19 | CH$_3$(CH$_2$)$_3$ | CHO | H | H | H | H | F | H | H | H |
| IV-20 | CH$_3$(CH$_2$)$_4$ | CHO | H | H | H | H | F | H | H | H |
| IV-21 | CH$_3$(CH$_2$)$_5$ | CHO | H | H | H | H | F | H | H | H |
| IV-22 | (CH$_3$)$_2$CHCH$_2$ | CHO | H | H | H | H | F | H | H | H |
| IV-23 | CH$_3$C≡CCH$_2$ | CHO | H | H | H | H | F | H | H | H |
| IV-24 | CH$_3$(CH$_2$)$_4$ | CF$_3$CO | H | CH$_3$S | H | H | H | H | H | H |
| IV-25 | 3-pyridylmethyl | CHO | H | H | H | H | H | H | H | H |
| IV-26 | C$_6$H$_5$(CH$_2$)$_2$ | CHO | H | H | H | H | F | H | H | H |
| IV-27 | CH$_3$(CH$_2$)$_3$ | CH$_3$CO | H | H | H | H | H | H | H | H |
| IV-28 | CH$_3$(CH$_2$)$_4$ | CH$_3$O$_2$C | H | H | H | H | H | H | H | H |
| IV-29 | CH$_3$(CH$_2$)$_4$ | (CH$_3$)$_3$CO$_2$C | H | H | H | H | H | H | H | H |
| IV-30 | CH$_3$(CH$_2$)$_4$ | PhCH$_2$O$_2$C | H | H | H | H | H | H | H | H |
| IV-31 | CH$_3$(CH$_2$)$_4$ | AllylO$_2$C | H | H | H | H | H | H | H | H |
| IV-32 | CH$_3$(CH$_2$)$_3$ | CH$_3$O$_2$C | H | H | H | H | H | H | H | H |
| IV-33 | CH$_3$(CH$_2$)$_5$ | CH$_3$O$_2$C | H | H | H | H | H | H | H | H |
| IV-34 | CH$_3$ | (CH$_3$)$_3$CO$_2$C | H | H | H | H | H | H | H | H |
| IV-35 | CH$_3$CH$_2$ | (CH$_3$)$_3$CO$_2$C | H | H | H | H | H | H | H | H |
| IV-36 | CH$_3$(CH$_2$)$_2$ | (CH$_3$)$_3$CO$_2$C | H | H | H | H | H | H | H | H |
| IV-37 | CH$_3$(CH$_2$)$_5$ | (CH$_3$)$_3$CO$_2$C | H | H | H | H | H | H | H | H |
| IV-38 | CH$_3$(CH$_2$)$_6$ | (CH$_3$)$_3$CO$_2$C | H | H | H | H | H | H | H | H |
| IV-39 | CH$_3$(CH$_2$)$_7$ | (CH$_3$)$_3$CO$_2$C | H | H | H | H | H | H | H | H |
| IV-40 | C$_6$H$_5$(CH$_2$)$_3$ | (CH$_3$)$_3$CO$_2$C | H | H | H | H | H | H | H | H |
| IV-41 | CH$_3$ | CH$_3$(CH$_2$)$_3$O$_2$C | H | H | H | H | H | H | H | H |
| IV-42 | CH$_3$(CH$_2$)$_4$ | (CH$_3$)$_3$CO$_2$C | H | (CH$_3$)$_2$CH | H | H | H | H | H | H |
| IV-43 | CH$_3$OCH$_2$ | (CH$_3$)$_3$CO$_2$C | H | H | H | H | H | H | H | H |
| IV-44 | CH$_3$CH$_2$OCH$_2$ | (CH$_3$)$_3$CO$_2$C | H | H | H | H | H | H | H | H |
| IV-45 | CH$_3$CH$_2$OC(=O)CH$_2$ | (CH$_3$)$_3$CO$_2$C | H | H | H | H | H | H | H | H |
| IV-46 | CH$_3$C(=O)OCH$_2$ | (CH$_3$)$_3$CO$_2$C | H | H | H | H | H | H | H | H |
| IV-47 | CH$_3$C(=O)OCH$_2$ | (CH$_3$)$_3$CO$_2$C | H | (CH$_3$)$_3$C | H | H | H | H | H | H |
| IV-48 | CH$_3$C(=O)OCH$_2$ | (CH$_3$)$_3$CO$_2$C | H | CH$_3$CH$_2$O | H | H | H | H | H | H |

TABLE 2

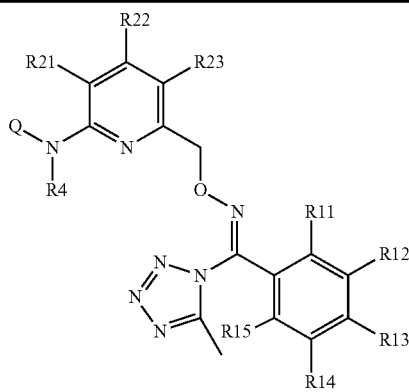

| Compound No. | Q | R4 | R21 | R22 | R23 | R11 | R12 | R13 | R14 | R15 |
|---|---|---|---|---|---|---|---|---|---|---|
| V-1 | CH$_3$(CH$_2$)$_4$ | H | H | H | H | H | H | H | H | H |
| V-2 | CH$_3$(CH$_2$)$_4$ | CHO | H | H | H | H | H | H | H | H |

TABLE 3

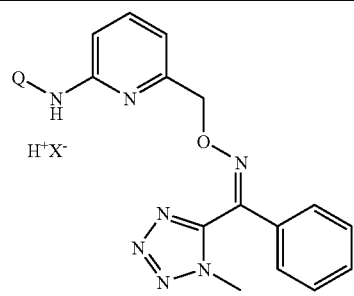

| Compound No. | Q | R4 | R21 | R11 | R12 | R13 | R14 | R15 |
|---|---|---|---|---|---|---|---|---|
| VI-1 | CH$_3$(CH$_2$)$_4$ | H | H | H | H | H | H | H |
| VI-2 | C$_6$H$_5$(CH$_2$)$_2$ | H | H | H | H | H | H | H |

TABLE 4

| Compound No. | Q | X$^-$ |
|---|---|---|
| VII-1 | CH$_3$ | 1-naphthoate (CO$_2^-$) |

TABLE 4-continued

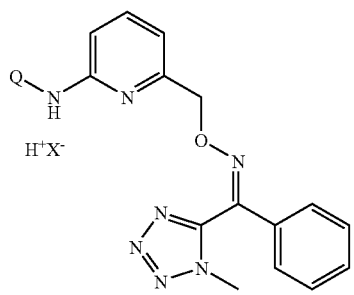

| Compound No. | Q | X$^-$ |
|---|---|---|
| VII-2 | CH$_3$(CH$_2$)$_3$ | 2-hydroxybenzoate (salicylate) |
| VII-3 | CH$_3$(CH$_2$)$_4$ | Cl$^-$ |
| VII-4 | CH$_3$(CH$_2$)$_4$ | CF$_3$SO$_3^-$ |
| VII-5 | C$_6$H$_5$(CH$_2$)$_3$ | Cl$^-$ |
| VII-6 | 4-MeOC$_6$H$_4$(CH$_2$)$_2$ | 4-CH$_3$C$_6$H$_4$SO$_3^-$ |

A tetrazoyloxime derivative or salt thereof represented by the aforementioned formula (1) (to be referred to as a "compound of the present invention") has superior antimicrobial effects against a wide spectrum of types of mold fungi such as Oomycetes species, Ascomycetes species, Deuteromycetes species and Basidiomycetes species. Thus, a composition having as an active ingredient thereof a compound of the present invention can be used to control various plant diseases occurring during cultivation of agricultural and horticultural crops such as flowering plants, grasses and forage grasses by seed treatment, foliar spraying, soil application or paddy water application and the like.

Examples of crops in which plant diseases can be controlled along with their pathogen include:

Beets:
  *Cercospora* leaf spot (*Cercospora beticola*)
  *Aphanomyces* root rot (*Aphanomyces cochlioides*)

Peanuts:
  Brown leaf spot (*Mycosphaerella arachidis*)
  Leaf spot (*Mycosphaerella berkeleyi*)
Cucumbers:
  Powdery mildew (*Sphaerotheca fuliginea*)
  Gummy stem blight (*Mycosphaerella melonis*)
  Stem rot (*Sclerotinia sclerotiorum*)
  Gray mold (*Botrytis cinerea*)
  Scab (*Cladosporium cucumerinum*)
  Downy mildew (*Pseudoperonospora cubensis*)
Tomatoes:
  Gray mold (*Botrytis cinerea*)
  Leaf mold (*Cladosporium fulvum*)
  Cottony leak (*Phythium aphanidermatum*)
  Late blight (*Phytophtora infestans*)
Eggplants:
  Gray mold (*Botrytis cinerea*)
  Black rot (*Corynespora melongenae*)
  Powdery mildew (*Erysiphe cichoracearum*)
Spinach:
  Damping-off (*Pythium ultimum*)
Strawberries:
  Gray mold (*Botrytis cinerea*)
  Powdery mildew (*Sphaerotheca aphanis*)
Onions:
  Neck rot (*Botrytis allii*)
  Gray mold (*Botrytis cinerea*)
Kidney beans:
  Stem rot (*Sclerotinia sclerotiorum*)
Gray mold (*Botrytis cinerea*)
  Apples:
    Powdery mildew (*Podosphaera leucotricha*)
    Scab (*Venturia inaequalis*)
    Blossom blight (*Monilinia mali*)
Persimmons:
  Powdery mildew (*Phyllactinia kakicola*)
  Anthracnose (*Gloeosporium kaki*)
  Angular leaf spot (*Cercospora kaki*)
Peaches and cherries:
  Brown rot (*Monilinia fructicola*)
Grapes:
  Gray mold (*Botrytis cinerea*)
  Powdery mildew (*Uncinula necator*)
  Ripe rot (*Glomerella cingulata*)
  Downy mildew (*Plasmopara viticola*)
Pears:
  Scab (*Venturia nashicola*)
  Rust (*Gymnosporangium asiaticum*)
  Black spot disease (*Alternaria kikuchiana*)
Tea:
  Gray blight (*Pestalotia theae*)
  Anthracnose (*Collectotrichum theae-sinensi*) citrus
  Scab (*Elsinoe faweette*)
  Blue mold (*Penicillium italicum*)
  Green mold (*Penicillium digitatum*)
  Gray mold (*Botrytis cinerea*)
Barley:
  Powdery mildew (*Erysiphe graminis* f. sp. *hordei*)
  Loose smut (*Ustilago nuda*)
Wheat:
  Scab (*Gibberella zeae*)
  Rust (*Puccinia recondita*)
  Spot blotch (*Cochliobolus sativus*)
  Glume blotch (*Leptosphaeria nodorum*)
  Eye spot (*Pseudocercosporella herpotrichoides*)
  Powdery mildew (*Erysiphe graminis* f. sp. *tritici*)
  Fusarium snow mold (*Micronectriella nivalis*)
  Browning root rot (*Pythium iwayamai*)

Rice:
  Blast (*Pyricularia oryzae*)
  Sheath blight (*Rhizoctonia solani*)
  Bakanae disease (*Gibberella fujikuroi*)
  Brown spot (*Cochliobolus niyabeanus*)
  Seedling blight (*Pythium graminicolum*)
Soybeans:
  Purple blotch (*Cercospora kikuchii*)
  Downy mildew (*Peronospora manshurica*)
  Phytophthora rot (*Phytophthora sojae*)
Potatoes:
  Late blight (*Phytophthora infestans*)
  Clubroot (*Plasmodiophora brassicae*)
Tobacco:
  Sclerotinia stem-rot (*Sclerotinia sclerotiorum*)
  Powdery mildew (*Erysiphe cichoracearum*)
Tulips:
  Gray mold (*Botrytis cinerea*)
Bentgrass:
  Sclerotinia snow blight (*Selerotinia borealis*)
  Pythium red blight (*Pythium aphanidermatum*)
Orchardgrass:
  Powdery mildew (*Erysiphe graminis*)

In addition, various pathogens have recently developed resistance to phenylamide fungicides and strobilurin fungicides resulting in inadequate efficacy of these fungicides, thereby creating the need for effective fungicides against resistant organisms as well. The compounds of the present invention also have superior antimicrobial effects against resistance organisms in addition to pathogens that are sensitive to these fungicides.

For example, the compounds of the present invention are effective against potato and tomato late blight (*Phytophthora infestans*), cucumber downy mildew (*Pseudoperonospora cubensis*) and grape downy mildew (*Plasmopara viticola*), which are resistant to metalaxyl, as well as sensitive organisms.

Moreover, the compounds of the present invention are effective against cucumber downy mildew (*Pseudoperonospora cubensis*) and grape downy mildew (*Plasmopara viticola*), which demonstrate resistance to strobilurin fungicides (such as kresoxim-methyl or azoxystrobin), as well as sensitive organisms.

Examples of diseases for which application is preferable include numerous types of diseases caused by Oomycetes species, such as grape downy mildew (*Plasmopara viticola*), cucubitaceous downy mildew (*Pseudoperonospora cubensis*), potato and tomato late blight (*Phytophthora infestans*), turf *Pythium* red blight (*Pythium aphanidermatum*) or beet black root disease (*Aphanomyces cochlioides*).

The compounds of the present invention can also be used as anti-fouling agents for preventing aquatic organisms from adhering to boat bottoms, fishing nets and other objects in contact with water.

In addition, some intermediate compounds of the compounds of the present invention also demonstrate antimicrobial activity.

Moreover, the compounds of the present invention can also be used as antimicrobial or anti-mold agents for walls, bathtubs, shoes or clothing by incorporating in paint or fibers and the like.

2) Plant Disease Control Agent

A second aspect of the present invention is a plant disease control agent that contains as an active ingredient thereof at least one type of compound of the present invention.

The plant disease control agent of the present invention may contain only a compound of the present invention without containing other ingredients, or may adopt a form able to be adopted by ordinary agricultural chemicals, namely a wettable powder, granules, powder, emulsion, aqueous solution, suspension or flowable agent.

Examples of additives and carriers able to be added to the plant disease control agent used for the purpose of solid agents include botanical powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

In addition, examples of additives when intending to produce a liquid formulation include petroleum residues such as kerosene, xylene and solvent naphtha, and solvents such a cyclohexane, cyclohexanone, N,N-dimethylformamide, dimethylsulfoxide, alcohol, acetone, trichloroethylene, methyl isobutyl ketone, mineral oil, vegetable oil and water.

Moreover, a surfactant can be used in these preparations as necessary to obtain a uniform and stable form.

Examples of surfactants used include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether, and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates, and isobutylene-maleic hydrate copolymer.

Normally, the amount of active ingredient in the preparations is preferably 0.5 to 95% by weight and more preferably 2 to 70% by weight based on the total weight of the composition (preparation).

In the case the plant disease control agent of the present invention is a wettable powder, emulsion or flowable agent, it can be used in the form of a suspension or emulsion by diluting to a prescribed concentration with water. In addition, in the case it is in the form of a powder of granules, it can be used by spraying directly onto plants.

Although a compound of the present invention or plant disease control agent of the present invention is naturally adequately effective even if used alone, it can also be used by mixing with one or more types of various fungicides, insecticides, miticides or synergists.

Typical examples of fungicides, insecticides, miticides and plant growth regulators able to be used by mixing with a compound of the present invention or plant disease control agent of the present invention are indicated below.

Fungicides:
Copper agents: basic copper chloride, basic copper sulfate
Sulfur agents: thiuram, zineb, maneb, mancozeb, ziram, propineb, polycarbamate
Polyhaloalkylthio agents: captan, folpet, dichlorofluranid
Organic chlorine agents: chlorothalonil, fthalide
Organic phosphorous agents: IBP, EDDP, triclofos-methyl, pyrazophos, fosetyl
Benzimidazole agents: thiophanate-methyl, benomyl, carbendazim, thiabendazole
Dicarboximide agents: iprodione, procymidone, vinclozoline, fluoroimide
Carboxyamide agents: oxycarboxin, mepronil, flutolanil, tecloftalum, trichlamide, pencycuron
Acylanaline agents: metalaxil, oxadixyl, furalaxyl
Methoxyacrylate agents: kresoxim-methyl, azoxystrobin, metominostrobin
Anilinopyrimidine agents: andopurine, mepanipyrim, pyrimethanil, cyprodinil
SBI agents: triadimefon, triadimenol, bitertanol, myclobutanil, hexaconazole, propiconazole, triflumizole, procloraz, pefurazoate, fenarimol, pyrifenox, triforine, flusilazol, etaconazole, diclobutrazol, fluotrimazole, flutriafen, penconazole, diniconazole, imazalil, tridemorph, fenpropimorph, buthiobate, epoxyconazole, metconazole
Strobilurin-based agents: strobilurin-A, metominostrobin, kresoxim-methyl, trifloxystrobin, dimoxystrobin, orysastrobin
Antibiotic agents: polyoxin, blasticidin 5, kasugamycin, validamycin, dihydrostreptomycin sulfate
Other agents: Propamocarb hydrochloride, quintozene, hydroxyisoxazole, methasulfocarb, anilazine, isoprothiolane, probenazole, chinomethionate, dithianone, dinocap, diclomezine, phermzone, fluazinam, pyroquilone, tricyclazole, oxolinic acid, dithianone, iminoctadine acetate, cymoxanil, pyrrolnitrin, methasulfocarb, diethofencarb, binapacryl, lecithin, sodium bicarbonate, fenaminosulf, dodine, dimethomorph, phenazin oxide, carpropamide, flusulfamide, fludioxonil, famoxadone, fluopicolide, mandipropamide, benthiavalicarb-isopropyl, ethaboxam, cyazofamid
Insecticides/Miticides:
Organic phosphorous and carbamate-based insecticides: fenthion, fenitrothion, diazinon, chlopyrifos, ESP, vamidothion, phenthoate, dimethoate, formothion, marathon, trichlorfon, thiometon, phosmet, dichlorphos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb
Pyrethroid insecticides: permethrin, dipermethrin, deltamethrin, fenvalerate, fenpropathrin, pyrethrin, allethrin, tetramethrin, resmethrin, dimethrin, propathrin, phenothrin, protolin, fluvalinate, cyfluthrin, cyhalothrin, flucythrinate, etofenprox, cycloprothin, tralomethrin, silafluofen, flufenprox, acrinathrin
Benzoylurea and other insecticides: diflubenzuron, chlorofluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, microbial agricultural drugs such as BT or insect pathogenic viruses
Nematicides:
Fenamiphos, fosthiazate
Miticides: Chlorobenzilate, phenisobromolate, dicofol, amitraz, BPPS, benzomate, hexythiazox, fenbutatinoxide, polynactin, quinomethionate, CPCBS, tetradifon, abamectin, milbemectin, clofentezine, cyhexatin, piridaben, fenpyroximate, tebufenpyrad, pyrimidifen, fenothiocarb, dienochlor
Plant growth regulators:
Gibberellin (such as gibberellin A3, gibberellin A4 or gibberellin A7), IAA, NAA

EXAMPLES

The following provides a more detailed explanation of the present invention through examples thereof. However, the present invention is not limited to the following examples.

Example 1

0.33 g of sodium hydride (oil component: 50 to 72% by weight) were suspended in 20 ml of N,N-dimethylformamide followed by the addition thereto of 1.69 g (8.3 mmol) of (Z)-(1-methyl-1H-tetrazol-5-yl)phenylmethanone oxime while cooling with ice and stirring the entire amount for 20 minutes. Next, 10 ml of an N,N-dimethylformamide solution containing 2.05 g (8.5 mmol) of 6-chloromethyl-2-(N-formyl-N-n-pentylamino)pyridine were added to the resulting reaction mixture followed by stirring the entire amount for 3.5 hours at room temperature. After adding aqueous ammonium chloride solution to the reaction mixture, the reaction mixture was extracted with ethyl acetate. After washing the organic layer with water, the organic layer was dried with anhydrous magnesium sulfate followed by distilling off the solvent. The resulting residue was purified by silica gel column chromatography (developing solvent: n-hexane/ethyl acetate=5/1 to 3/1 (v/v)) to obtain 2.60 g of (Z)-(1-methyl-1-tetrazol-5-yl)phenylmethanone-O-(6-(N-formyl-N-n-pentylamino)pyridin-2-ylmethyl) oxime (melting point: 68 to 69° C.) (compound no. IV-3 in the previous tables).

Example 2

0.5 ml of 3 M hydrochloric acid were added to 5 ml of an ethyl acetate solution of the (Z)-(1-methyl-1H-tetrazol-5-yl)phenylmethanone-O-(6-(N-formyl-N-n-pentylamino)pyridin-2-ylmethyl) oxime obtained in Example 1 followed by stirring for 5 hours at room temperature. The pH of the reaction liquid was adjusted to pH 7 by adding aqueous sodium carbonate solution thereto. After extracting with ethyl acetate, the product was washed with water and dried with anhydrous magnesium sulfate followed by distilling off the solvent. The resulting residue was purified by silica gel column chromatography (developing solvent: n-hexane/ethyl acetate=2/1 (v/v)) to obtain 0.14 g of (Z)-(6-n-pentylaminopyridin-2-yl)methoxyimino-(1-methyl-1H-tetrazol-5-yl)phenylmethane (compound no. 1-6 in the previous tables).

The physical property or $^1$H-NMR data (300 MHz, CDCl$_3$, TMS, δppm) of compounds produced in the same manner as Examples 1 and 2 are shown in Table 5. The compound numbers correspond to the compound numbers shown in the previous tables. Furthermore, "br-s" refers to a broad singlet, while "br-t" refers to a broad triplet.

TABLE 5

| Compound No. shown in TABLES 1-4 | Physical property values [ ]: melting point(° C.), nD: refractive index, nD (measurement temperature, ° C.) | $^1$H-NMR |
|---|---|---|
| I-1 | [107-108] | |
| I-2 | | 1.25 (t, 3H, J = 7.2 Hz), 3.27 (q, 2H, J = 7.2 Hz), 3.40 (s, 3H), 4.44 (br-s, 1H), 5.20 (s, 2H), 6.40 (d, 1H, J = 8.4 Hz), 6.52 (d, 1H. J = 7.2 Hz), 7.42-7.50 (m, 4H), 7.53 (d, 2H, J = 4.5 Hz) |
| I-3 | | 0.99 (t, 3H, J = 7.2 Hz), 1.65 (sept, 2H, J = 7.2 Hz), 3.20 (q, 2H, J = 7.2 Hz), 3.99 (s, 3H), 4.52 (m, 3H), 5.20 (s, 2H), 6.30 (d, 1H, J = 8.4 Hz), 6.51 (d, 1H, J = 7.5 Hz), 7.45-7.50 (m, 4H), 7.53 (d, 2H, J = 4.5 Hz) |
| I-4 | | 0.95 (t, 3H, J = 7.4 Hz), 1.36-1.49 (m, 2H), 1.56-1.66 (m, 2H), 3.23 (m, 2H), 3.98 (s, 3H), 5.22 (s, 2H), 6.32 (d, 1H, J = 8.4 Hz), 6.51 (d, 1H, J = 7.2 Hz), 7.35-7.46 (m, 4H), 7.52-7.55 (m, 2H) |
| I-5 | [88-90] | |
| I-6 | | 0.91 (m, 3H), 1.36 (m, 4H), 1.58 (m, 2H), 3.23 (q, 2H, J = 6.9 Hz), 3.99 (s, 2H), 4.49 (br-s, 1H), 5.19 (s, 2H), 6.30 (d, 1H, J = 8.1 Hz), 6.51 (d, 1H, J = 6.9 Hz), 7.29-7.44 (m, 6H), 7.53 (d, 2H, J = 4.5 Hz) |
| I-7 | [104-107] | |
| I-8 | | 0.87 (t, 3H, J = 6.6 Hz), 1.18-1.44 (m, 6H), 1.58 (m, 2H), 3.22 (q, 2H, J = 6.9 Hz), 3.99 (s, 3H), 4.52 (br-s, 1H), 5.19 (s, 2H), 6.29 (d, 1H, J = 8.1 Hz), 6.51 (d, 1H, J = 7.2 Hz), 7.25-7.44 (m, 4H), 7.54 (d, 2H, J = 4.5 Hz) |
| I-9 | | 0.89 (t, 3H, J = 6.6 Hz), 1.29 (m, 8H), 1.57 (m, 2H), 3.21 (q, 2H, J = 7.2 Hz), 3.99 (s, 3H), 4.50 (br-s, 1H), 5.19 (s, 2H), 6.29 (d, 1H, J = 8.7 Hz), 6.50 (d, 1H, J = 7.2 Hz), 7.24-7.46 (m, 4H), 7.54 (d, 2H, J = 4.5 Hz) |
| I-10 | | 0.88 (t, 3H, J = 6.3 Hz), 1.26 (m, 10H), 1.60 (m, 2H), 3.21 (q, 2H, J = 6.9 Hz), 3.99 (s, 3H), 4.49 (br-s, 1H), 5.19 (s, 2H), 6.29 (d, 1H, J = 8.4 Hz), 6.50 (d, 1H, J = 7.2 Hz), 7.30-7.45 (m, 4H), 7.54 (d, 2H, J = 4.5 Hz) |
| I-11 | | 3.90-3.95 (m, 2H), 3.99 (s, 3H), 4.61 (br-s, 1H), 5.13-5.29 (m, 4H), 5.89-5.98 (m, 1H), 6.32 (d, 1H, J = 8.1 Hz), 6.54 (d, 1H, J = 7.2 Hz), 7.34-7.46 (m, 4H), 7.52-7.55 (m, 2H) |
| I-12 | [122-124] | |
| I-13 | | 1.79 (t, 3H, J = 2.6 Hz), 4.00 (s, 3H), 4.02-4.06 (m, 2H), 4.58 (br-s, 1H), 5.21 (s, 2H), 6.38 (d, 1H, J = 8.4 Hz), 6.58 (d, 1H, J = 7.2 Hz), 7.34-7.55 (m, 4H), 7.53-7.55 (m, 2H) |
| I-14 | | 3.97 (s, 3H), 4.06-4.17 (m, 2H), 4.59 (br-s, 1H), 5.22 (s, 2H), 6.42 (d, 1H, J = 8.2 Hz), 6.64 (d, 1H, J = 7.3 Hz), 7.34-7.48 (m, 4H), 7.54 (d, 2H, J = 7.8 Hz) |

TABLE 5-continued

| Compound No. shown in TABLES 1-4 | Physical property values [ ]: melting point(° C.), nD: refractive index, nD (measurement temperature, ° C.) | $^1$H-NMR |
|---|---|---|
| I-15 | | 4.00 (s, 3H), 4.34 (d, 2H, J = 6.6 Hz), 4.60 (br-s, 1H), 5.27 (s, 2H), 6.46 (d, 1H, J = 7.5 Hz), 6.70 (d, 1H, J = 7.2 Hz), 7.34-7.56 (m, 6H) |
| I-16 | | 2.71 (t, 2H, J = 6.2 Hz), 3.67 (m, 2H, J = 6.2 Hz), 3.98 (s, 3H), 4.74 (br-s, 1H), 5.22 (s, 2H), 6.36 (d, 1H, J = 8.1 Hz), 6.57 (d, 1H, J = 7.2 Hz), 7.35-7.47 (m, 4H), 7.51-7.54 (m, 2H) |
| I-17 | | 1.92-2.01 (m, 2H), 2.44 (t, 2H, J = 7.1 Hz), 3.48 (q, 2H, J = 6.5 Hz), 4.00 (s, 3H), 4.52 (br-s, 1H), 5.21 (s, 2H), 6.33 (d, 1H, J = 8.7 Hz), 6.55 (d, 1H, J = 7.2 Hz), 7.34-7.46 (m, 4H), 7.52-7.55 (m, 2H) |
| I-18 | | 1.74-1.79 (m, 4H), 2.38-2.43 (m, 2H), 3.34-3.38 (m, 2H), 3.99 (s, 3H), 4.47 (br-s, 1H), 5.21 (s, 2H), 6.30 (d, 1H, J = 8.1 Hz), 6.53 ((d, 1H, J = 7.5 Hz), 7.34-7.46 (m, 4H), 7.52-7.55 (m, 2H) |
| I-19 | [101-102] | |
| I-20 | | 2.91 (t, 2H, J = 7.1 Hz), 3.51-3.57 (m, 2H), 3.97 (s, 3H), 4.54 (br-s, 1H), 5.20 (s, 2H), 6.30 (d, 1H, J = 8.4 Hz), 6.53 (d, 1H, J = 7.3 Hz), 7.21-7.55 (m, 11H) |
| I-21 | [108-109] | |
| I-22 | | 1.61-1.77 (m, 4H), 2.66 (t, 2H, J = 7.3 Hz), 3.23-3.29 (m, 2H), 3.98 (s, 3H), 5.21 (s, 2H), 6.30 (d, 1H, J = 8.6 Hz), 6.52 (d, 1H, J = 7.1 Hz), 7.16-7.20 (m, 3H), 7.25-7.30 (m, 2H), 7.34-7.46 (m, 4H), 7.52-7.55 (m, 2H) |
| I-23 | | 3.94 (s, 3H), 4.59 (d, 2H, J = 6.0 Hz), 4.93 (t, 1H, J = 6.0 Hz), 5.22 (s, 2H), 6.29 (d, 1H, J = 8.2 Hz), 6.58 (d, 1H, J = 7.3 Hz), 7.34-7.58 (m, 10H) |
| I-24 | | 2.85 (t, 2H, J = 7.0 Hz), 3.49 (td, 2H, J = 7.0, 5.8 Hz), 3.80 (s, 3H), 3.97 (s, 3H), 4.51 (br-s, 1H), 5.20 (s, 2H), 6.30 (d, 1H, J = 8.4 Hz), 6.53 (d, 1H, J = 7.3 Hz), 6.85 (d, 2H, J = 8.4 Hz), 7.13 (d, 2H, J = 8.4 Hz), 7.34-7.46 (m, 4H), 7.54 (d, 2H, J = 7.3 Hz) |
| I-25 | | 1.19-1.28 (m, 9H), 3.98 (s, 3H), 4.33 (d, 2H, J = 7.2 Hz), 5.22 (s, 2H), 6.39 (d, 1H, J = 7.5 Hz), 6.54 (d, 1H, J = 7.5 Hz), 7.34-7,46 (m, 4H), 7.52-7.55 (m, 2H) |
| I-26 | | 1.28 (t, 3H, J = 7.2 Hz), 4.00 (s, 3H), 4.12 (d, 2H, J = 5.7 Hz), 4.22 (q, 2H, J = 7.2 Hz), 4.94 (br-s, 1H), 5.20 (s, 2H), 6.39 (d, 1H, J = 8.1 Hz), 6.58 (d, 1H, J = 7.2 Hz), 7.34-7.46 (m, 4H), 7.52-7.55 (m, 2H) |
| I-27 | [75-77] | |
| I-28 | | 1.89-2.05 (m, 2H), 2.89 (br-s, 1H), 3.29-3.37 (m, 4H), 3.95 (br-s, 1H), 4.00 (s, 3H), 5.00 and 5.17 (maybe two isomeric br-s, 1H), 5.20 (s, 2H), 6.31 (d, 1H, J = 8.4 Hz), 6.50 (d, 1H, J = 7.3 Hz), 7.33-7.55 (m, 6H) |
| I-29 | | 3.96 (s, 3H), 4.64 (d, 2H, J = 5.4 Hz), 5.23 (s, 2H), 5.58 (br-s, 1H), 6.38 (d, 1H, J = 8.4 Hz), 6.55 (d, 1H, J = 7.5 Hz), 7.16-7.20 (m, 1H), 7.30-7.46 (m, 5H), 7.52-7.55 (m, 2H), 7.61-7.67 (m, 1H), 8.56 (d, 1H, J = 5.1 Hz) |
| I-30 | | 3.96 (s, 3H), 4.64 (d, 2H, J = 5.5 Hz), 4.85 (br-t, 1H, J = 5.5 Hz), 5.22 (s, 2H), 6.31 (d, 1H, J = 8.4 Hz), 6.56 (d, 1H, J = 7.5 Hz), 7.22-7.26 (m, 1H), 7.35-7.55 (m, 6H), 7.66 (d, 1H, J = 7.8 Hz), 8.51 (d, 1H, J = 4.8 Hz), 8.61 (s, 1H) |
| I-31 | | 3.97 (s, 3H), 4.43 (d, 2H, J = 5.3 Hz), 4.45 (br-s, 2H), 5.23 (s, 2H), 5.50 (br-s, 1H), 6.37 (d, 1H, J = 8.6 Hz), 6.39 (d, 1H, J = 8.2 Hz), 6.55 (d, 1H, J = 7.3 Hz), 6.65 (dd, 1H, J = 7.4, 0.6 Hz), 7.34-7.49 (m, 5H), 7.53-7.56 (m, 2H) |
| I-32 | | 3.93 (s, 3H), 4.56 (d, 2H, J = 6.6 Hz), 4.93 (br-t, 1H, J = 6.6 Hz), 5.20 (s, 2H), 6.30 (d, 1H, J = 8.4 Hz), 6.56 (d, 1H, J = 7.2 Hz), 7.25-7.27 (m, 1H), 7.35-7.47 (m, 4H), 7.51-7.55 (m, 2H), 7.63-7.67 (m, 1H), 8.38-8.39 (m, 1H) |
| I-33 | | 3.96 (s, 3H), 4.53 (d, 2H, J = 6.0 Hz), 4.84 (br-t, 1H, J = 6.0 Hz), 5.21 (s, 2H), 6.30 (d, 1H, J = 8.4 Hz), 6.56 (d, 1H, J = 7.2 Hz), 7.25-7.27 (m, 1H), 7.35-7.47 (m, 4H), 7.51-7.55 (m, 2H), 7.63-7.67 (m, 1H), 8.38-8.39 (m, 1H) |
| I-34 | | 3.97 (s, 3H), 4.43 (d, 2H, J = 5.1 Hz), 4.45 (d, 2H, J = 5.5 Hz), 4.52 (br-s, 2H), 5.22 (s, 2H), 5.51 (br-t, 1H, J = 5.5 Hz), 5.65 (br-t, 1H, J = 5.1 Hz), 6.31 (d, 1H, J = 7.9 Hz), |

TABLE 5-continued

| Compound No. shown in TABLES 1-4 | Physical property values [ ]: melting point(° C.), nD: refractive index, nD (measurement temperature, ° C.) | $^1$H-NMR |
|---|---|---|
| | | 6.38 (d, 1H, J = 8.2 Hz), 6.38 (d, 1H, J = 8.2 Hz), 6.55 (d, 1H, J = 7.5 Hz), 6.57 (d, 1H, J = 7.5 Hz), 6.68 (dd, 1H, J = 7.4, 0.6 Hz), 7.34-7.43 (m, 6H), 7.52-7.56 (m, 2H) |
| I-35 | | 2.93 (s, 6H), 3.96 (s, 3H), 4.36 (d, 2H, J = 4.5 Hz), 5.22 (s, 2H), 6.32 (d, 1H, J = 8.4 Hz), 6.54 (d, 1H, J = 7.2 Hz), 6.70 (d, 2H, J = 8.7 Hz), 7.21 (d, 2H, J = 8.7 Hz), 7.34-7.43 (m, 4H), 7.52-7.55 (m, 2H) |
| I-36 | | 3.80 (s, 3H), 3.95 (s, 3H), 4.42 (d, 2H, J = 5.6 Hz), 4.81 (t, 1H, J = 5.6 Hz), 5.22 (s, 2H), 6.31 (d, 1H, J = 8.4 Hz), 6.55 (d, 1H, J = 7.1 Hz), 6.86 (d, 2H, J = 8.8 Hz), 7.26 (d, 2H, J = 8.8 Hz), 7.35-7.46 (m, 3H), 7.52-7.56 (m, 2H) |
| II-1 | | 0.91 (m, 3H), 1.35 (m, 4H), 1.59 (m, 2H), 3.19 (m, 2H), 4.01 (s, 3H), 5.34 (s, 2H), 6.30 (d, 1H, J = 8.7 Hz), 7.31-7.46 (m, 5H), 7.58 (m, 2H) |
| II-2 | | 0.92 (t, 3H, J = 7.1 Hz), 1.34-1.39 (m, 4H), 1.61 (t, 2H, J = 7.2 Hz), 3.20 (q, 2H, J = 6.5 Hz), 4.01 (s, 3H), 4.60 (br-s, 1H), 5.14 (s, 2H), 6.29 (d, 1H, J = 1.5 Hz), 6.53 (d, 1H, J = 1.5 Hz), 7.35-7.45 (m, 3H), 7.53 (dd, 2H, J = 8.4, 1.6 Hz) |
| II-3 | | 0.91 (t, 3H, J = 7.1 Hz), 1.32-1.40 (m, 4H), 1.56-1.65 (m, 2H), 2.43 (s, 3H), 3.16-3.23 (m, 2H), 4.00 (s, 3H), 4.49 (br-t, 1H), 5.16 (s, 2H), 6.08 (d, 1H, J = 1.5 Hz), 6.35 (d, 1H, J = 1.5 Hz), 7.34-7.47 (m, 3H), 7.54 6.08 (d, 2H, J = 6.8 Hz) |
| II-4 | | 0.91 (t, 3H, J = 7.0 Hz), 1.35-1.40 (m, 4H), 1.63 (t, 2H, J = 7.0 Hz), 2.83 (d, 3H, J = 4.9 Hz), 3.13 (t, 2H, J = 7.0 Hz), 4.01 (s, 3H), 4.24 (br-s, 1H), 5.15 (s, 2H), 5.36 (d, 1H, J = 1.8 Hz), 5.76 (d, 1H, J = 1.8 Hz), 7.34-7.44 (m, 3H), 7.52-7.55 (m, 2H) |
| II-5 | | 0.91 (t, 3H, J = 7.0 Hz), 1.20 (d, 6H, J = 7.0 Hz), 1.35-1.40 (m, 4H), 1.59-1.63 (m, 2H), 2.76 (septet, 1H, J = 7.0 Hz), 3.19-3.25 (m, 2H), 4.00 (s, 3H), 4.43 (br-s, 1H), 5.18 (s, 2H), 6.15 (s, 1H), 6.41 (s, 1H), 7.34-7.43 (m, 3H), 7.53-7.57 (m, 2H) |
| II-6 | | 0.90 (t, 3H, J = 7.0 Hz), 1.32-1.37 (m, 4H), 1.56-1.61 (m, 2H), 3.16-3.23 (m, 2H), 4.03 (s, 3H), 4.55 (br-s, 1H), 5.34 (s, 2H), 6.23 (d, 1H, J = 8.8 Hz), 7.37-7.43 (m, 3H), 7.51 (d, 1H, J = 8.8 Hz), 7.55-7.58 (m, 2H) |
| II-7 | | 0.91 (t, 3H, J = 7.0 Hz), 1.33-1.39 (m, 4H), 1.57-1.64 (m, 2H), 3.41 (dt, 2H, J = 7.1, 5.7 Hz), 4.00 (s, 3H), 5.00 (br-s, 1H), 5.23 (s, 2H), 6.38 (d, 1H, J = 7.9 Hz), 1H), 7.34-7.47 (m, 3H), 7.52-7.56 (m, 3H) |
| II-8 | | 0.89 (t, 3H, J = 7.0 Hz), 1.28-1.34 (m, 4H), 1.58 (tt, 2H, J = 7.3, 7.1 Hz), 3.37 (td, 2H, J = 7.3, 5.3 Hz), 4.02 (s, 3H), 5.00 (t, 1H, J = 5.3 Hz), 5.33 (s, 2H), 7.34-7.47 (m, 3H), 7.55-7.58 (m, 2H), 7.72 (s, 1H) |
| II-9 | | 0.89-0.94 (m, 3H), 1.35-1.39 (m, 4H), 1.56-1.63 (m, 2H), 2.22 (s, 3H), 3.17-3.23 (m, 2H), 4.00 (s, 3H), 4.47 (br-s, 1H), 5.17 (s, 2H), 6.12 (s, 1H), 6.36 (s, 1H), 7.34-7.46 (m, 3H) 7.53-7.56 (m, 2H) |
| II-10 | | 0.91 (t, 3H, J = 7.0 Hz), 1.34-1.39 (m, 4H), 1.55-1.65 (m, 2H), 2.17 (s, 3H), 3.18 (t, 2H, J = 6.8 Hz), 3.95 (s, 3H), 4.41 (br-s, 1H), 5.26 (s, 2H), 6.30 (d, 1H, J = 8.4 Hz), 7.23 (d, 1H, J = 8.4 Hz), 7.34-7.43 (m, 3H), 7.52-7.55 (m, 2H) |
| II-11 | | 0.92 (t, 3H, J = 7.1 Hz), 1.25 (s, 9H), 1.36-1.40 (m, 4H), 1.59-1.62 (m, 2H), 3.20-3.27 (m, 2H), 4.00 (s, 3H), 4.43 (br-s, 1H), 5.20 (s, 2H), 6.26 (d, 1H, J = 1.5 Hz), 6.54 (d, 1H, J = 1.5 Hz), 7.37-7.43 (m, 3H), 7.54-7.57 (m, 2H) |
| II-12 | | 0.92 (t, 3H, J = 6.9 Hz), 1.36-1.41 (m, 4H), 1.59-1.67 (m, 2H), 3.23-3.30 (m, 2H), 3.98 (s, 3H), 4.57 (br-t, 1H, J = 5.2 Hz), 5.21 (s, 2H), 6.41 (d, 1H, J = 8.4 Hz), 6.82-6.95 (m, 1H), 7.20-7.23 (m, 1H), 7.32-7.42 (m, 7H), 7.49-7.52 (m, 2H) |
| II-13 | | 0.89 (t, 3H, J = 6.9 Hz), 1.27-1.31 (m, 4H), 1.52-1.59 (m, 2H), 3.39 (td, 2H, J = 7.3, 5.4 Hz), 4.05 (s, 3H), 4.53 (t, 1H, J = 5.4 Hz), 5.23 (s, 2H), 7.15 (s, 1H), 7.18 (d, 2H, J = 8.2 Hz), 7.34-7.46 (m, 9H), 7.52-7.55 (m, 2H) |

TABLE 5-continued

| Compound No. shown in TABLES 1-4 | Physical property values [ ]: melting point(° C.), nD: refractive index, nD (measurement temperature, ° C.) | ¹H-NMR |
|---|---|---|
| II-14 | | 0.89-0.93 (m, 3H), 1.35-1.39 (m, 4H), 1.56-1.63 (m, 2H), 3.14-3.20 (m, 2H), 3.78 (s, 3H), 4.01 (s, 3H), 4.52 (br-s, 1H), 5.15 (s, 2H), 5.76 (s, 1H), 6.13 (s, 1H), 7.34-7.55 (m, 5H) |
| II-15 | | 0.91 (t, 3H, J = 7.0 Hz), 1.34-1.41 (m, 4H), 1.39 (t, 3H, J = 7.1 Hz), 1.58-1.63 (m, 2H), 3.13-3.19 (m, 2H), 4.01 (s, 3H), 4.02 (q, 2H, 7.1 Hz), 4.46 (br-s, 1H), 5.15 (s, 2H), 5.74 (d, 1H, J = 1.8 Hz), 6.12 (d, 1H, J = 1.8 Hz), 7.37-7.44 (m, 3H), 7.52-7.55 (m, 2H) |
| II-16 | | 0.89-0.93 (m, 3H), 1.32 (d, 6H, J = 6.0 Hz), 1.34-1.41 (m, 4H), 1.58-1.62 (m, 2H), 3.11-3.18 (m, 2H), 4.01 (s, 3H), 4.44 (br-s, 1H), 4.56 (sept, 1H, J = 6.0 Hz), 5.14 (s, 2H), 5.74 (s, 1H), 6.10 (s, 1H), 7.34-7.55 (m, 5H) |
| II-17 | | 0.91 (t, 3H, J = 7.1 Hz), 1.23 (t, 3H, J = 7.0 Hz), 1.34-1.39 (m, 4H), 1.55-1.63 (m, 2H), 3.12-3.19 (m, 2H), 3.58 (q, 2H, J = 7.0 Hz), 3.75-3.78 (m, 2H), 4.00 (s, 3H), 4.09-4.12 (m, 2H), 4.80 (br-s, 1H), 5.14 (s, 2H), 5.80 (d, 1H, J = 2.0 Hz), 6.15 (d, 1H, J = 2.0 Hz), 7.34-7.44 (m, 3H), 7.52-7.55 (m, 2H) |
| II-18 | | 0.91 (t, 3H, J = 6.9 Hz), 1.35-1.40 (m, 4H), 1.65-1.67 (m, 2H), 3.01 (s, 6H), 3.11-3.17 (m, 2H), 4.00 (s, 3H), 5.21 (s, 2H), 5.35 (d, 1H, J = 1.8 Hz), 5.91 (d, 1H, J = 1.8 Hz), 7.35-7.48 (m, 3H), 7.52-7.55 (m, 2H) |
| II-19 | | 0.93 (t, 3H, J = 7.0 Hz), 1.18 (d, 6H, J = 7.0 Hz), 1.19 (d, 6H, J = 7.0 Hz), 1.37-1.40 (m, 4H), 1.62-1.66 (m, 2H), 2.70-2.80 (m, 2H), 3.22-3.26 (m, 2H), 3.98 (s, 3H), 4.38 (d, 2H, J = 5.2 Hz), 4.61 (br-s, 1H), 5.21 (s, 2H), 5.52 (t, 1H, J = 5.2 Hz), 6.11 (s, 1H), 6.24 (s, 1H), 6.43 (s, 1H), 6.46 (s, 1H), 7.34-7.43 (m, 3H), 7.54-7.58 (m, 2H) |
| III-1 | | 0.89-0.94 (m, 3H), 1.35-1.40 (m, 4H), 1.61-1.64 (m, 2H), 3.19-3.26 (q, 2H, J = 5.7 Hz), 4.08 (s, 3H), 4.52 (br-s, 1H), 5.22 (s, 2H), 6.30 (d, 1H, J = 8.4 Hz), 6.50 (d, 1H, J = 6.0 Hz), 7.00-7.05 (m, 1H), 7.20-7.30 (m, 1H), 7.38-7.50 (m, 2H), 7.70-7.76 (m, 1H) |
| III-2 | | 0.95 (t, 3H, J = 7.2 Hz), 1.38-1.48 (m, 2H), 1.55-1.65 (m, 2H), 3.23 (q, 2H, J = 7.2 Hz), 4.00 (s, 3H), 4.48 (br-s, 1H), 5.20 (s, 2H), 6.31 (d, 1H, J = 8.4 Hz), 6.51 (d, 1H, J = 7.2 Hz), 7.09-7.16 (m, 1H), 7.21-7.43 (m, 4H) |
| III-3 | | 0.93 (m, 3H), 1.37 (m, 4H), 1.57 (m, 2H), 3.23 (m, 2H), 4.00 (s, 3H), 4.50 (br-s, 1H), 5.23 (s, 2H), 6.30 (d, 1H, J = 8.1 Hz), 6.50 (d, 1H, J = 7.2 Hz), 7.10-7.45 (m, 5H) |
| III-4 | | 0.90 (t, 3H, J = 6.8 Hz), 1.31-1.41 (m, 6H), 1.56-1.65 (m, 2H), 3.22 (q, 2H, J = 6.9 Hz), 4.00 (s, 3H), 4.49 (br-s, 1H), 5.20 (s, 2H), 6.31 (d, 1H, J = 8.4 Hz), 6.51 (d, 1H, J = 7.2 Hz), 7.10-7.16 (m, 1H), 7.22-7.43 (m, 4H) |
| III-5 | | 0.98 (d, 6H, J = 6.9 Hz), 1.83-1.92 (m, 1H), 3.06 (t, 2H, J = 6.3 Hz), 4.00 (s, 3H), 4.58 (br-s, 1H), 5.20 (s, 2H), 6.31 (d, 1H, J = 8.4 Hz), 6.50 (d, 1H, J = 7.2 Hz), 7.09-7.16 (m, 1H), 7.22-7.43 (m, 4H) |
| III-6 | | 2.91 (t, 2H, J = 6.9 Hz), 3.54 (q, 2H, J = 6.9 Hz), 3.97 (s, 3H), 4.51 (br-s, 1H), 5.21 (s, 2H), 6.31 (d, 1H, J = 8.1 Hz), 6.52 (d, 1H, J = 7.2 Hz), 7.09-7.16 (m, 1H), 7.21-7.43 (m, 9H) |
| III-7 | | 1.80 (t, 3H, J = 2.4 Hz), 4.01 (s, 3H), 4.02-4.07 (m, 2H), 4.59 (br-s, 1H), 5.22 (s, 2H), 6.40 (d, 1H, J = 8.1 Hz), 6.58 (d, 1H, J = 7.2 Hz), 7.10-7.16 (m, 1H), 7.22-7.46 (m, 4H) |
| III-8 | | 0.88-0.94 (m, 3H), 1.33-1.41 (m, 4H), 1.58-1.66 (m, 2H), 3.19-3.26 (m, 2H), 4.12 (s, 3H), 4.50 (br-s, 1H), 5.25 (s, 2H), 6.31 (d, 1H, J = 7.8 Hz), 6.53 (d, 1H, J = 6.9 Hz), 6.91-6.99 (m, 2H), 7.34-7.44 (m, 2H) |
| IV-1 | | 0.92 (t, 3H, J = 7.2 Hz), 1.36 (m, 2H), 1.60 (m, 2H), 3.92 (t, 2H, J = 7.5 Hz), 4.01 (s, 3H), 5.34 (s, 2H), 6.94 (d, 1H, J = 7.8 Hz), 7.05 (d, 1H, J = 7.5 Hz), 7.33-7.59 (m, 6H), 9.25 (s, 1H) |
| IV-2 | | 0.89 (d, 6H, J = 6.6 Hz), 1.92-2.03 (m, 1H), 3.80 (d, 2H, J = 7.5 Hz), 4.02 (s, 3H), 5.35 (s, 2H), 6.96 (d, 1H, J = 8.4 Hz), 7.06 (d, 1H, J = 7.5 Hz), 7.35-7.51 (m, 5H), 7.71 (t, 1H, J = 8.0 Hz), 9.24 (s, 1H) |

TABLE 5-continued

| Compound No. shown in TABLES 1-4 | Physical property values [ ]: melting point(° C.), nD: refractive index, nD (measurement temperature, ° C.) | $^1$H-NMR |
|---|---|---|
| IV-3 | | 0.88 (t, 3H, J = 6.6 Hz), 1.31 (m, 4H), 1.60 (m, 2H), 3.91 (t, 2H, J = 7.5 Hz), 4.01 (s, 3H), 5.34 (s, 2H), 6.93 (d, 1H, J = 8.1 Hz), 7.05 (d, 1H, J = 7.5 Hz), 7.31-7.56 (m, 6H), 9.25 (s, 1H) |
| IV-4 | | 0.86 (t, 3H, J = 6.6 Hz), 1.26 (m, 6H), 1.59 (m, 2H), 3.91 (t, 2H, J = 7.8 Hz), 4.02 (s, 3H), 5.34 (s, 2H), 6.93 (d, 1H, J = 8.4 Hz), 7.05 (d, 1H, J = 7.5 Hz), 7.29-7.56 (m, 5H), 7.71 (t, 1H, J = 7.8 Hz), 9.25 (s, 1H) |
| IV-5 | | 0.86 (t, 3H, J = 7.2 Hz), 1.26 (m, 8H), 1.56 (m, 2H), 3.91 (t, 2H, J = 7.2 Hz), 4.02 (s, 3H), 5.34 (s, 2H), 6.94 (d, 1H, J = 8.1 Hz), 7.05 (d, 1H, J = 7.5 Hz), 7.31-7.56 (m, 5H), 7.71 (t, 1H, J = 8.1 Hz), 9.25 (s, 1H) |
| IV-6 | | 4.01 (s, 3H), 4.53-4.55 (m, 2H), 5.16-5.21 (m, 2H), 5.34 (s, 2H), 5.79-5.92 (m, 1H), 6.93 (d, 1H, J = 8.4 Hz), 7.05 (d, 1H, J = 7.5 Hz), 7.36-7.53 (m, 5H), 7.70 (t, 1H, J = 7.8 Hz), 9.43 (s, 1H) |
| IV-7 | | 2.16 (t, 1H, J = 2.5 Hz), 4.01 (s, 3H), 4.70 (d, 2H, J = 2.5 Hz), 5.36 (s, 2H), 7.09 (m, 2H), 7.26-7.54 (m, 5H), 7.74 (t, 1H, J = 8.0 Hz), 9.35 (t, 1H) |
| IV-8 | | 1.75 (t, 3H, J = 2.5 Hz), 4.02 (s, 3H), 4.61 (d, 2H, J = 2.5 Hz), 5.35 (s, 2H), 7.07 (m, 2H), 7.36-7.54 (m, 5H), 7.75 (t, 1H, J = 8.0 Hz), 9.40 (s, 1H) |
| IV-9 | | 3.95 (s, 3H), 5.16 (s, 2H), 5.34 (s, 2H), 6.85 (d, 1H, J = 8.4 Hz), 7.01 (d, 1H, J = 7.8 Hz), 7.21-7.52 (m, 10H), 7.60 (t, 1H, J = 7.4 Hz), 9.52 (s, 1H) |
| IV-10 | | 2.91 (t, 2H, J = 8.0 Hz), 4.00 (s, 3H), 4.17-4.20 (m, 2H), 5.35 (s, 2H), 6.88 (t, 1H, J = 8.7 Hz), 7.03 (t, 1H, J = 7.5 Hz), 7.19-7.36 (m, 5H), 7.39-7.54 (m, 5H), 7.66 (t, 1H, J = 8.0 Hz), 9.19 (s, 1H) |
| IV-11 | [90-92] | |
| IV-12 | | 1.23-1.28 (m, 3H), 3.98 (s, 3H), 4.08-4.22 (m, 2H), 4.70 (s, 2H), 5.32 (s, 2H), 7.00 (d, 1H, J = 8.4 Hz), 7.08 (d, 1H, J = 7.8 Hz), 7.35-7.52 (m, 5H), 7.72 (t, 1H, J = 8.0 Hz), 9.24 (s, 1H) |
| IV-13 | | 4.02 (s, 3H), 4.91 (s, 2H), 5.39 (s, 2H), 7.11-7.18 (m, 2H), 7.36-7.53 (m, 5H), 7.80 (t, 1H, J = 8.0 Hz), 9.12 (s, 1H) |
| IV-14 | | 3.98 (s, 3H), 5.24 (s, 2H), 5.32 (s, 2H), 7.01-7.04 (m, 2H), 7.14-7.67 (m, 9H), 8.51-8.53 (m, 1H), 9.65 (s, 1H) |
| IV-15 | | 3.98 (s, 3H), 5.17 (s, 2H), 5.33 (s, 2H), 6.85 (d, 1H, J = 8.1 Hz), 7.05 (d, 1H, J = 7.8 Hz), 7.17 (d, 2H, J = 5.7 Hz), 7.36-7.51 (m, 5H), 7.64 (t, 1H, J = 8.1 Hz), 8.50 (d, 2H, J = 5.7 Hz), 9.45 (s, 1H) |
| IV-16 | | 3.98 (s, 3H), 5.17 (s, 2H), 5.35 (s, 2H), 6.93 (d, 1H, J = 8.4 Hz), 7.05 (d, 1H, J = 7.5 Hz), 7.21-7.26 (m, 1H), 7.36-7.51 (m, 5H), 7.61-7.71 (m, 2H), 8.41 (d, 1H, J = 2.4 Hz), 9.24 (s, 1H) |
| IV-17 | | 0.85 (t, 3H, J = 7.2 Hz), 1.26 (m, 4H), 1.53 (m, 2H), 3.86 (t, 2H, J = 7.8 Hz), 4.00 (s, 3H), 5.38 (s, 2H), 7.18 (d, 1H, J = 7.8 Hz), 7.26-7.50 (m, 6H), 7.81 (t, 1H, J = 7.8 Hz) |
| IV-18 | | 0.85 (t, 3H, J = 6.6 Hz), 1.27 (m, 2H, 1.54 (m, 4H), 3.85 (t, 2H, J = 7.8 Hz), 4.00 (s, 3H), 5.38 (s, 2H), 7.17 (d, 1H, J = 8.4 Hz), 7.26-7.51 (m, 6H), 7.81 (t, 1H, J = 7.8 Hz) |
| IV-19 | | 0.92 (t, 3H, J = 7.4 Hz), 1.31-1.41 (m, 2H), 1.53-1.63 (m, 2H), 3.92 (t, 2H, J = 7.4 Hz), 4.02 (s, 3H), 5.35 (s, 2H), 6.95 (d, 1H, J = 8.1 Hz), 7.04 (d, 1H, J = 7.5 Hz), 7.12-7.39 (m, 4H), 7.72 (t, 1H, J = 8.0 Hz), 9.25 (s, 1H) |
| IV-20 | | 0.88 (t, 3H, J = 6.9 Hz), 1.24-1.33 (m, 4H), 1.57-1.62 (m, 2H), 3.91 (t, 2H, J = 7.7 Hz), 4.03 (s, 3H), 5.35 (s, 2H), 6.95 (d, 1H, J = 8.1 Hz), 7.04 (d, 1H, J = 7.5 Hz), 7.12-7.23 (m, 2H), 7.32-7.39 (m, 2H), 7.72 (t, 1H, J = 8.0 Hz), 9.26 (s, 1H) |
| IV-21 | | 0.86 (t, 3H, J = 6.9 Hz), 1.29 (s, 6H), 1.55-1.59 (m, 2H), 3.91 (t, 2H, J = 7.7 Hz), 4.02 (s, 3H), 5.35 (s, 2H), 6.95 (d, 1H, J = 7.8 Hz), 7.03 (d, 1H, J = 7.5 Hz), 7.13-7.38 (m, 4H), 7.72 (t, 1H, J = 8.0 Hz), 9.25 (s, 1H) |
| IV-22 | | 0.89 (d, 6H, J = 6.9 Hz), 1.92-2.02 (m, 1H), 3.80 (d, 2H, J = 7.8 Hz), 4.03 (s, 3H), 5.36 (s, 2H), 6.97 (d, 1H, J = 8.1 Hz), 7.05 (d, 1H, J = 7.5 Hz), 7.12-7.39 (m, 4H), 7.72 (t, 1H, J = 8.0 Hz), 9.25 (s, 1H) |
| IV-23 | | 1.76 (t, 3H, J = 2.4 Hz), 4.03 (s, 3H), 4.61 (d, 2H, J = 2.4 Hz), 5.36 (s, 2H), 7.06-7.38 (m, 6H), 7.76 (t, 1H. J = 8.0 Hz), 9.39 (s, 1H) |

TABLE 5-continued

| Compound No. shown in TABLES 1-4 | Physical property values [ ]: melting point(° C.), nD: refractive index, nD (measurement temperature, ° C.) | ¹H-NMR |
|---|---|---|
| IV-24 | | 0.86 (t, 3H, J = 7.0 Hz), 1.26-4.32 (m, 4H), 1.50-1.60 (m, 2H), 2.51 (s, 3H), 3.83 (t, 2H, J = 7.7 Hz), 4.01 (s, 3H), 5.33 (s, 2H), 6.94 (s, 1H), 7.01 (s, 1H), 7.36-7.53 (m, 5H) |
| IV-25 | | 3.98 (s, 3H), 5.19 (s, 2H), 5.35 (s, 2H), 6.91 (d, 1H, J = 8.4 Hz), 7.04 (d, 1H, J = 7.8 Hz), 7.18-7.22 (m, 1H), 7.35-7.52 (m, 5H), 7.63-7.70 (m. 2H), 8.47-8.49 (m, 1H), 8.60 (d, 1H, J = 2.1 Hz), 9.35 (s, 1H) |
| IV-26 | nD22.2 1.5989 | |
| IV-27 | nD23.4 1.5817 | |
| IV-28 | | 0.86 (t, 3H, J = 6.9 Hz), 1.22-1.35 (m, 4H), 1.52-1.63 (m, 2H), 3.77 (s, 3H), 3.93 (t, 2H, J = 7.5 Hz), 3.98 (s, 3H), 5.33 (s, 2H), 7.02 (d, 1H, J = 7.2 Hz), 7.35-7.40 (m, 3H), 7.42-7.54 (m, 3H), 7.65 (dd, 1H, J = 8.1, 7.5 Hz) |
| IV-29 | | 0.88 (t, 3H, J = 6.9 Hz), 1.23-1.34 (m, 4H), 1.51 (s, 9H), 1.54-1.65 (m, 2H), 3.92 (t, 2H, J = 7.2 Hz), 3.99 (s, 3H), 5.30 (s, 2H), 6.99 (d, 1H, J = 7.2 Hz), 7.32-7.54 (m, 6H), 7.61 (dd, 1H, J = 7.8. 7.5 Hz) |
| IV-32 | | 0.88 (t, 3H, J = 7.2 Hz), 1.23-1.35 (m, 2H), 1.51-1.58 (m, 2H), 3.77 (s, 3H), 3.94 (t, 2H, J = 7.5 Hz), 3.99 (s, 3H), 5.33 (s, 2H), 7.01 (d, 1H, J = 7.5 Hz), 7.35-7.40 (m, 3H), 7.44-7.54 (m, 3H), 7.65 (dd, 1H, J = 7.8. 7.8 Hz) |
| IV-33 | | 0.86 (t, 3H, J = 6.9 Hz), 1.25-1.32 (m, 6H), 1.50-1.62 (m, 2H), 3.77 (s, 3H), 3.94 (t, 2H, J = 7.5 Hz), 3.98 (s, 3H), 5.33 (s, 2H), 7.02 (d, 1H, J = 7.8 Hz), 7.35-7.40 (m, 3H), 7.44-7.54 (m, 3H), 7.65 (dd, 1H, J = 7.8. 7.8 Hz) |
| IV-34 | | 1.52 (s, 9H), 3.37 (s, 3H), 3.99 (s, 3H), 5.32 (s, 2H), 6.93-6.99 (m, 1H), 7.34-7.55 (m, 5H), 7.61-7.64 (m, 2H) |
| IV-35 | | 1.19 (t, 3H, J = 6.9 Hz), 1.51 (s, 9H), 3.94 (t, 2H, J = 6.9 Hz), 3.98 (s, 3H), 5.32 (s, 2H), 6.95 (d, 1H, J = 7.2 Hz), 7.26-7.45 (m, 3H), 7.55-7.65 (m, 4H) |
| IV-36 | | 0.86 (t, 3H, J = 7.8 Hz), 1.50 (s, 9H), 1.59 (m, 2H), 3.86 (t, 2H, J = 7.5 Hz), 3.97 (s, 3H), 5.32 (s, 2H), 6.96 (d, 1H, J = 7.2 Hz), 7.28-7.42 (m, 5H), 7.51 (d, 1H, J = 6.9 Hz), 7.61 (t, 1H, J = 8.1 Hz) |
| IV-37 | | 0.86 (t, 3H, J = 6.3 Hz), 1.26 (m, 6H), 1.50 (s, 9H), 1.56 (m, 2H), 3.89 (t, 2H, J = 7.5 Hz), 3.97 (s, 3H), 5.32 (s, 2H), 6.95 (d, 1H, J = 7.2 Hz), 7.30-7.43 (m, 5H), 7.53 (d, 1H, J = 7.2 Hz), 7.61 (t, 1H, J = 7.5 Hz) |
| IV-38 | | 0.86 (t, 3H, J = 6.6 Hz), 1.26 (m, 8H), 1.50 (s, 9H), 1.47-1.64 (m, 2H), 3.89 (t, 2H, J = 7.5 Hz), 3.97 (s, 3H), 5.32 (s, 2H), 6.96 (d, 1H, J = 7.2 Hz), 7.31-7.45 (m, 5H), 7.51 (d, 1H, J = 7.2 Hz), 7.63 (t, 1H, J = 7.5 Hz) |
| IV-39 | | 0.87 (t, 3H, J = 6.6 Hz), 1.25 (m, 10H), 1.50 (s, 9H), 1.45-1.62 (m, 2H), 3.89 (t, 2H, J = 7.2 Hz), 3.97 (s, 3H), 5.32 (s, 2H), 6.96 (d, 1H, J = 6.9 Hz), 7.29-7.47 (m, 5H), 7.53 (d, 1H, J = 6.9 Hz), 7.61 (t, 1H, J = 8.1 Hz) |
| IV-40 | | 1.48 (s, 9H), 1.95 (tt, 2H, J = 7.8, 7.5 Hz), 2.62 (t, 2H, J = 7.8 Hz), 3.93 (s, 3H), 3.93-3.97 (m, 2H), 5.29 (s, 2H), 6.96 (dd, 1H, J = 7.3, 0.5 Hz), 7.12-7.18 (m, 3H), 7.22-7.27 (m, 2H), 7.34-7.47 (m, 3H), 7.51-7.63 (m, 4H) |
| IV-41 | | 0.95 (t, 3H, J = 7.4 Hz), 1.41 (tq, 2H, J = 7.6, 7.4 Hz), 1.67 (tt, 3H, J = 7.6, 6.7 Hz), 3.42 (s, 3H), 3.99 (s, 3H), 4.20 (t, 2H, J = 6.7 Hz), 5.33 (s, 2H), 6.99 (d, 1H, J = 7.4 Hz), 7.35-7.73 (m, 7H) |
| IV-42 | | 0.86 (t, 3H, J = 7.0 Hz), 1.23 (d, 6H, J = 7.0 Hz), 1.24-1.33 (m, 4H), 1.50 (s, 9H), 1.56-1.63 (m, 2H), 2.88 (sept, 1H, J = 7.0 Hz), 3.86 (t, 2H, J = 7.6 Hz), 3.98 (s, 3H), 5.30 (s, 2H), 6.84 (s, 1H), 7.33 (s, 1H), 7.35-7.47 (m, 3H), 7.53-7.56 (m, 2H) |
| IV-43 | | 1.51 (s, 9H), 3.36 (s, 3H), 3.97 (s, 3H), 5.33 (s, 2H), 5.34 (s, 2H), 7.06 (d, 1H, J = 7.5 Hz), 7.35-7.45 (m, 4H), 7.50-7.53 (m, 2H), 7.67 (dd, 1H, J = 8.1, 7.5 Hz) |
| IV-44 | | 1.15 (t, 3H, J = 7.1 Hz), 1.50 (s, 9H), 3.58 (q, 2H, J = 7.1 Hz), 3.96 (s, 3H), 5.34 (s, 2H), 5.38 (s, 2H), 7.06 (d, 1H, J = 7.5 Hz), 7.35-7.47 (m, 4H), 7.52 (d, 2H, J = 8.6 Hz), 7.67 (dd, 1H, J = 8.1, 7.5 Hz) |
| IV-45 | | 1.25 (t, 3H, J = 7.1 Hz), 1.52 (s, 9H), 3.93 (s, 3H), 4.17 (q, 2H, J = 7.1 Hz), 4.68 (s, 2H), 5.26 (s, 2H), 6.97 (d, |

TABLE 5-continued

| Compound No. shown in TABLES 1-4 | Physical property values [ ]: melting point(° C.), nD: refractive index, nD (measurement temperature, ° C.) | $^1$H-NMR |
|---|---|---|
| | | 1H, J = 7.5 Hz), 7.35-7.45 (m, 3H), 7.50-7.53 (m, 2H), 7.64 (dd, 1H, J = 8.3, 7.5 Hz), 7.82 (d, 1H, J = 8.3 Hz) |
| IV-46 | | 1.52 (s, 9H), 2.05 (s, 3H), 3.98 (s, 3H), 5.33 (s, 2H), 5.95 (s, 2H), 7.06 (d, 1H, J = 7.5 Hz), 7.35-7.54 (m, 6H), 7.67 (dd, 1H, J = 8.4, 7.5 Hz) |
| IV-47 | | 1.30 (s, 9H), 1.51 (s, 9H), 2.04 (s, 3H), 3.99 (s, 3H), 5.31 (s, 2H), 5.92 (s, 2H), 7.06 (s, 1H), 7.35-7.55 (m, 6H) |
| IV-48 | | 1.41 (t, 3H, J = 7.1 Hz), 1.51 (s, 9H), 2.04 (s, 3H), 3.99 (s, 3H), 4.07 (q, 2H, J = 7.1 Hz), 5.26 (s, 2H), 5.93 (s, 2H), 6.57 (d, 1H, J = 2.0 Hz), 7.03 (d, 1H, J = 2.0 Hz), 7.35-7.54 (m, 5H) |
| V-1 | | 0.89 (m, 3H), 1.37 (m, 4H), 1.60 (m, 2H), 2.51 (s, 3H), 3.23 (m, 2H), 4.52 (br-s, 1H), 5.18 (s, 2H), 6.30 (d, 1H, J = 8.0 Hz), 6.49 (d, 1H, J = 7.2 Hz), 7.33-7.55 (m, 6H) |
| V-2 | | 0.87 (t, 3H, J = 7.2 Hz), 1.32 (m, 4H), 1.60 (m, 2H), 2.52 (s, 3H), 3.91 (t, 2H, J = 7.5 Hz), 5.32 (s, 2H), 6.94 (d, 1H, J = 8.1 Hz), 7.03 (d, 1H, J = 7.5 Hz), 7.37-7.5 (m, 5H), 7.72 (t, 1H, J = 7.5 Hz), 9.26 (s, 1H) |
| VI-1 | | 0.90 (m, 3H), 1.32 (m, 4H), 1.66 (m, 2H), 3.20 (m, 2H), 3.98 (s, 3H), 5.13 (s, 2H), 5.28 (br-s, 1H), 6.41 (s, 1H), 7.32-7.46 (m, 3H), 7.54 (m, 2H) |
| VI-2 | | 2.91 (t, 2H, J = 7.2 Hz), 3.47 (dd, 2H, J = 6.3, 12.3 Hz), 3.95 (s, 3H), 5.10 (s, 2H), 5.56 (br-s, 1H), 6.42 (s, 1H), 7.30-7.63 (m, 10H) |
| VII-1 | | 2.93 (s, 3H), 3.99 (s, 3H), 5.28 (s, 2H), 6.39 (d, 1H, J = 8.6 Hz), 6.55 (d, 1H, J = 7.3 Hz), 7.33-7.66 (m, 9H), 7.91 (d, 1H, J = 8.1 Hz), 8.05 (d, 1H, J = 8.2 Hz), 8.32 (dd, 1H, J = 7.3, 1.1 Hz), 9.05 (d, 1H, J = 8.8 Hz) |
| VII-2 | [113-114] | |
| VII-3 | [116-118] | |
| VII-4 | nD23.4 1.5386 | |
| VII-5 | [157-159] | |
| VII-6 | | 2.38 (s, 3H), 2.96 (t, 2H, J = 7.4 Hz), 3.48 (td, 2H, J = 7.4, 5.7 Hz), 3.76 (s, 3H), 3.96 (s, 3H), 5.40 (s, 2H), 6.55 (d, 1H, J = 10.1 Hz), 6.59 (d, 1H, J = 7.3 Hz), 6.80 (d, 2H, J = 8.8 Hz), 7.14 (d, 2H, J = 8.8 Hz), 7.20 (d, 2H, J = 8.1 Hz), 7.36-7.41 (m, 2H), 7.45-7.50 (m, 3H), 7.65-7.71 (m, 1H), 7.81 (d, 2H, J = 8.1 Hz), 9.28 (br-s, 1H) |

The following indicates several preparation examples of the plant disease control agent of the present invention. Additives and addition rates are not limited to those used in these examples, and can be changed over a wide range. The term "parts" used in the preparation examples refers to parts by weight.

Preparation Example 1

Wettable Powder

| Compound of present invention | 40 parts |
|---|---|
| Clay | 53 parts |
| Sodium dioctylsulfosuccinate | 4 parts |
| Sodium lignin sulfonate | 3 parts |

The above components were mixed and finely crushed to obtain a wettable powder containing 40% of the active ingredient.

Preparation Example 2

Emulsion

| Compound of present invention | 10 parts |
|---|---|
| Solvesso 200 | 53 parts |
| Cyclohexanone | 26 parts |
| Calcium dodecylbenzenesulfonate | 1 part |
| Polyoxyethylene alkyl allyl ether | 10 parts |

The above components were mixed and dissolved to obtain an emulsion containing 10% of the active ingredient.

Preparation Example 3

Powder

| | |
|---|---|
| Compound of present invention | 10 parts |
| Clay | 90 parts |

The above components were uniformly mixed and finely crushed to obtain a powder containing 10% of the active ingredient.

Preparation Example 4

Granules

| | |
|---|---|
| Compound of present invention | 5 parts |
| Clay | 73 parts |
| Bentonite | 20 parts |
| Sodium dioctylsulfosuceinate | 1 part |
| Potassium phosphate | 1 part |

The above components were crushed and mixed followed by the addition of water, mixing well, granulating and drying to obtain granules containing 5% of the active ingredient.

Preparation Example 5

Suspension

| | |
|---|---|
| Compound of present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components were mixed and wet-crushed to a particle size of 3 microns or less to obtain a suspension containing 10% of the active ingredient.

Preparation Example 6

Granulated Wettable Powder

| | |
|---|---|
| Compound of present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensate of sodium alkylbenzenesulfonate | 5 parts |

The above components were uniformly mixed and finely crushed followed by adding a suitable amount of water and mixing to form a clay-like substance. The clay-like substance was then granulated and then dried to obtain a granulated wettable powder containing 40% of the active ingredient.

Test Example

Tomato Late Blight Preventive Effect

Tomato seedlings (variety: Regina, 4th to 5th leaf term) cultivated in terracotta pots were sprayed with the emulsion of Preparation Example 2 described above at an active ingredient concentration of 100 ppm. After spraying, the plants were allowed to air dry at room temperature, and the test plants were inoculated by spraying with a suspension of zoosporangia of tomato late blight pathogen (*Phytophthora infestans*) and holding for 4 days in a high-humidity, constant temperature chamber (20° C.) at a light/dark cycle of 12 hours. The appearance of lesion on the leaves was compared with untreated plants to determine control effects. As a result, the following compounds showed a protective value of 70%. Furthermore, the compound numbers shown below correspond to the compound numbers shown in TABLES 1 to 4.

Compound Numbers:
I-1 to I-14, I-17 to I-26, I-29 to I-36, II-1 to II-7, II-10 to II-12, II-14 to II-19, III-1 to III-7, IV-1 to IV-6, IV-17 to IV-24, IV-26 to IV-28, IV-32, IV-43 to IV-48, V-1 to V-2, VI-1 to VI-2, VII-1 to VII-6

INDUSTRIAL APPLICABILITY

The plant disease control agent of the present invention containing a tetrazoyloxime derivative or salt thereof as an active ingredient thereof demonstrates superior control effects against plant diseases even at low doses while also eliminating concern over chemical damage to useful plants, thereby leading to completion of the present invention, thereby making it industrially useful.

The invention claimed is:

1. A tetrazoyloxime derivative, or salt thereof, represented by the following formula (1):

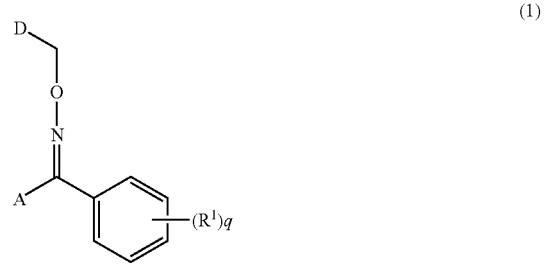

wherein, $R^1$ represents a halogen atom, q represents an integer of 0 to 2, $R^1$ may be the same or different when q is 2, A represents a tetrazoyl group represented by the following formula (2) or (3):

-continued

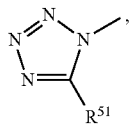

(wherein, $R^5$ and $R^{51}$ represent alkyl groups), and D represents a group represented by the following formula (4):

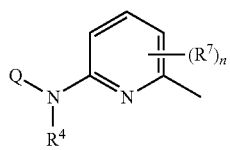

(wherein, $R^2$ represents a halogen atom, optionally substituted C1-C6 alkyl group, optionally substituted C1-C6 alkoxy group, optionally substituted C1-C6 alkylthio group, optionally substituted amino group or optionally substituted aryl group, n represents an integer of 0 to 3, $R^2$ may be the same or different when n is 2 or more, $R^4$ represents a hydrogen atom, and Q represents an optionally substituted C1-C20 alkyl group, optionally substituted C2-C20 alkenyl group, optionally substituted C2-C20 alkynyl group, optionally substituted C3-C8 cycloalkyl group, optionally substituted aralkyl group or optionally substituted heterocycloalkyl group), wherein the substituents of the optionally substituted C1-C20 alkyl group, optionally substituted C2-C20 alkenyl group, optionally substituted C2-C20 alkynyl group, optionally substituted C3-C8 cycloalkyl group, optionally substituted aralkyl group and optionally substituted heterocycloalkyl group are hydroxyl group; mercapto group; fluorine atom, chlorine atom, bromine atom, iodine atom; cyano group; isocyano group; nitro group; isocyanato group; isothiocyanato group; cyanato group; thiocyanato group; amino group, methylamino group, benzylamino group, anilino group, dimethylamino group, diethylamino group, phenylethylamino group, methylsulfonylamino group, ethylsulfonylamino group, n-propylsulfonylamino group, isopropylsulfonylamino group, n-butylsulfonylamino group, t-butylsulfonylamino group, phenylsulfonylamino group, piperazinylsulfonylamino group, methylcarbonylamino group, ethylcarbonylamino group, n-propylcarbonylamino group, isopropylcarbonylamino group, methoxycarbonylamino group, ethoxycarbonylamino group, n-propoxycarbonylamino group, isopropoxycarbonylamino group, fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 1,1,1-trifluoroethylsulfonylamino group, pentafluoroethylsulfonylamino group, bis(methylsulfonyl)amino group, bis(ethylsulfonyl)amino group, (ethylsulfonyl)(methylsulfonyl)amino group, bis(n-propylsulfonyl)amino group, bis(isopropylsulfonyl)amino group, bis(n-butylsulfonyl)amino group, bis(t-butylsulfonyl)amino group, bis(fluoromethylsulfonyl)amino group, bis(chloromethylsulfonyl)amino group, bis(bromomethylsulfonyl)amino group, bis(difluoromethylsulfonyl)amino group, bis(dichloromethylsulfonyl)amino group, bis(1,1-difluoroethylsulfonyl)amino group, bis(trifluoromethylsulfonyl)amino group, bis(1,1,1-trifluoroethylsulfonyl)amino group, bis(pentafluoroethylsulfonyl)amino group; methoxy group, ethoxy group, n-propoxy group, isopropoxy group, n-butoxy group, s-butoxy group, isobutoxy group, t-butoxy group; vinyloxy group, allyloxy group; ethynyloxy group, propargyloxy group; phenoxy group, 1-naphthoxy group; benzyloxy group, phenethyloxy group; 2-pyridyloxy group, 3-oxazolyloxy group; fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 1,1,1-trifluoroethoxy group, pentafluoroethoxy group, hepatafluoro-n-propoxy group; methylthiocarbonyl group, ethylthiocarbonyl group, n-propylthiocarbonyl group, isopropylthiocarbonyl group, n-butylthiocarbonyl group, isobutylthiocarbonyl group, s-butylthiocarbonyl group, t-butylthiocarbonyl group; hydrazino group, N'-phenylhydrazino group, N'-methoxycarbonylhydrazino group, N'-acetylhydrazino group, N'-methylhydrazino group; carboxyl group; methoxycarbonyl group, ethoxycarbonyl group, n-propoxycarbonyl group, isopropoxycarbonyl group, n-butoxycarbonyl group, t-butoxycarbonyl group; aminocarbonyl group, dimethylaminocarbonyl group, phenylaminocarbonyl group; hydrazinocarbonyl group, N'-methylhydrazinocarbonyl group, N'-phenylhydrazinocarbonyl group; phenyl group, 1-naphthyl group, 2-naphthyl group; furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group; pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group, 1,2,4-triazin-3-yl group; tetrahydrofuran-2-yl group, tetrahydropyran-4-yl group, piperidin-3-yl group, pyrrolidin-2-yl group, morpholino group, piperidino group, N-methylpiperazinyl group; N-methylaminoiminomethyl group, 1-N-phenyliminoethyl group, N-hydroxyiminomethyl group, N-methoxyiminomethyl group; N'-methylhydrazinocarbonyl group, N'-phenylhydrazinocarbonyl group, hydrazinocarbonyl group; aminocarbonyl group, dimethylaminocarbonyl group, N-phenyl-N-methylaminocarbonyl group; methylthio group, ethylthio group, t-butylthio group; vinylthio group, allylthio group; ethynylthio group, propargylthio group; phenylthio group, 4-chlorophenylthio group; 2-piperidylthio group, 3-pyridazinylthio group; benzylthio group, phenethylthio group; methylsulfonyl group, ethylsulfonyl group, t-butylsulfonyl group; allylsulfonyl group; propargylsulfonyl group; phenylsulfonyl group; 2-pyridylsulfonyl group, 3-pyridylsulfonyl group; benzylsulfonyl group, phenethylsulfonyl group; formyl group, acetyl group, propionyl group, chloroacetyl group, trifluoroacetyl group, trichloroacetyl group, cinnamoyl group, benzoyl group, 4-chlorobenzoyl group, 2-pyridylcarbonyl group, cyclohexylcarbonyl group; formyloxy group, acetyloxy group, propionyloxy group, chloroacetyloxy group, trifluoroacetyloxy group, trichloroacetyloxy group, cinnamoyloxy group, benzoyloxy group, 4-chlorobenzoyloxy group, 2-pyridylcarbonyloxy group, cyclohexylcarbonyloxy group.

2. A plant disease control agent that contains as an active ingredient thereof at least one type of tetrazoyloxime derivative or salt thereof according to claim 1.

* * * * *

UNITED STATES PATENT AND TRADEMARK OFFICE
CERTIFICATE OF CORRECTION

PATENT NO. : 8,084,613 B2  Page 1 of 1
APPLICATION NO. : 12/599854
DATED : December 27, 2011
INVENTOR(S) : Kobori et al.

It is certified that error appears in the above-identified patent and that said Letters Patent is hereby corrected as shown below:

On the cover of the patent
item (22) PCT Filed, change "May 14, 2007" to --May 14, 2008--

Signed and Sealed this
Twentieth Day of March, 2012

David J. Kappos
*Director of the United States Patent and Trademark Office*